(12) United States Patent
Harris et al.

(10) Patent No.: US 10,912,561 B2
(45) Date of Patent: Feb. 9, 2021

(54) BUTTRESS APPLIER CARTRIDGE FOR SURGICAL STAPLER HAVING END EFFECTOR WITH DEFLECTABLE CURVED TIP

(71) Applicant: ETHICON LLC, Guaynabo, PR (US)

(72) Inventors: Jason L. Harris, Lebanon, OH (US); Gregory J. Bakos, Mason, OH (US); Christopher J. Hess, Blue Ash, OH (US)

(73) Assignee: Ethicon LLC, Guaynabo, PR (US)

( * ) Notice: Subject to any disclaimer, the term of this patent is extended or adjusted under 35 U.S.C. 154(b) by 167 days.

(21) Appl. No.: 16/035,834

(22) Filed: Jul. 16, 2018

(65) Prior Publication Data

US 2020/0015817 A1 Jan. 16, 2020

(51) Int. Cl.
*A61B 17/072* (2006.01)

(52) U.S. Cl.
CPC ............ *A61B 17/07207* (2013.01); *A61B 2017/07221* (2013.01); *A61B 2017/07271* (2013.01)

(58) Field of Classification Search
CPC .... A61B 17/07207; A61B 2017/07221; A61B 2017/07271
USPC ................................................ 227/176.1, 19
See application file for complete search history.

(56) References Cited

U.S. PATENT DOCUMENTS

| 4,805,823 A | 2/1989 | Rothfuss |
| 5,014,899 A | 5/1991 | Presty et al. |
| 5,415,334 A | 5/1995 | Williamson et al. |
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A | 5/1998 | Francis et al. |
| 5,792,135 A | 8/1998 | Madhani et al. |
| 5,814,055 A | 9/1998 | Knodel et al. |
| 5,817,084 A | 10/1998 | Jensen |

(Continued)

FOREIGN PATENT DOCUMENTS

| EP | 2772202 WO | 9/2014 |
| WO | WO 2004/096057 | 11/2004 |

(Continued)

OTHER PUBLICATIONS

European Search Report dated Aug. 7, 2018 for Application No. 18157228.0, 8 pages.

(Continued)

*Primary Examiner* — Chelsea E Stinson
(74) *Attorney, Agent, or Firm* — Frost Brown Todd LLC

(57) ABSTRACT

An apparatus includes a housing a platform, and a first buttress assembly. The housing defines a gap configured to receive a portion of an end effector of a surgical stapler. The housing includes proximal and distal portions. A portion of the platform is exposed within the gap defined by the housing. The platform includes proximal and distal portions. The first buttress assembly is positioned on at least the proximal portion of the platform. The first buttress assembly is exposed in the gap defined by the housing. At least one of the distal portion of the platform or the distal portion of the housing includes a cavity configured to receive a curved distal tip of the end effector.

19 Claims, 20 Drawing Sheets

(56) References Cited

U.S. PATENT DOCUMENTS

| | | | |
|---|---|---|---|
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 6,939,358 | B2 | 9/2005 | Palacios et al. |
| 6,978,921 | B2 | 12/2005 | Shelton et al. |
| 7,000,818 | B2 | 2/2006 | Shelton et al. |
| 7,143,923 | B2 | 12/2006 | Shelton et al. |
| 7,303,108 | B2 | 12/2007 | Shelton |
| 7,367,485 | B2 | 5/2008 | Shelton et al. |
| 7,380,695 | B2 | 6/2008 | Doll et al. |
| 7,380,696 | B2 | 6/2008 | Shelton et al. |
| 7,404,508 | B2 | 7/2008 | Smith et al. |
| 7,434,715 | B2 | 10/2008 | Shelton et al. |
| 7,524,320 | B2 | 4/2009 | Tierney et al. |
| 7,644,848 | B2 | 1/2010 | Swayze et al. |
| 7,691,098 | B2 | 4/2010 | Wallace et al. |
| 7,721,930 | B2 | 5/2010 | McKenna et al. |
| 7,806,891 | B2 | 10/2010 | Nowlin et al. |
| 8,066,166 | B2 | 11/2011 | Demmy et al. |
| 8,136,711 | B2 | 3/2012 | Beardsly et al. |
| 8,210,411 | B2 | 7/2012 | Yates et al. |
| 8,348,123 | B2 | 1/2013 | Scirica et al. |
| 8,371,491 | B2 | 2/2013 | Huitema et al. |
| 8,403,195 | B2 | 3/2013 | Beardsly et al. |
| 8,403,196 | B2 | 3/2013 | Beardsly et al. |
| 8,408,439 | B2 | 4/2013 | Huang et al. |
| 8,453,914 | B2 | 6/2013 | Laurent et al. |
| 8,479,969 | B2 | 7/2013 | Shelton |
| 8,496,153 | B2 | 7/2013 | Demmy et al. |
| 8,573,461 | B2 | 11/2013 | Shelton et al. |
| 8,573,465 | B2 | 11/2013 | Shelton |
| 8,602,288 | B2 | 12/2013 | Shelton et al. |
| 8,616,431 | B2 | 12/2013 | Timm et al. |
| 8,690,039 | B2 | 4/2014 | Beardsly et al. |
| 8,714,429 | B2 | 5/2014 | Demmy |
| 8,783,541 | B2 | 7/2014 | Shelton et al. |
| 8,800,838 | B2 | 8/2014 | Shelton |
| 8,820,605 | B2 | 9/2014 | Shelton |
| 8,844,789 | B2 | 9/2014 | Shelton et al. |
| 8,844,790 | B2 | 9/2014 | Demmy et al. |
| 9,016,546 | B2 | 4/2015 | Demmy et al. |
| 9,039,736 | B2 | 5/2015 | Scirica et al. |
| 9,186,142 | B2 | 11/2015 | Fanelli et al. |
| 9,301,759 | B2 | 4/2016 | Spivey et al. |
| 9,433,416 | B2 | 9/2016 | Beardsly et al. |
| 9,517,065 | B2 | 12/2016 | Simms et al. |
| 9,522,004 | B2 | 12/2016 | Demmy |
| 9,597,078 | B2 | 3/2017 | Scirica et al. |
| 9,622,746 | B2 | 4/2017 | Simms et al. |
| 9,713,470 | B2 | 7/2017 | Scirica et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,420 | B2 | 12/2017 | Shelton, IV et al. |
| 9,839,421 | B2 | 12/2017 | Zerkle et al. |
| 9,913,642 | B2 | 3/2018 | Leimbach et al. |
| 9,936,952 | B2 | 4/2018 | Demmy |
| 9,936,968 | B2 | 4/2018 | Demmy et al. |
| 9,943,311 | B2 | 4/2018 | Scirica et al. |
| 10,080,564 | B2 | 9/2018 | Beardsly et al. |
| 10,166,023 | B2 | 1/2019 | Vendely et al. |
| 2004/0243151 | A1 | 12/2004 | Demmy et al. |
| 2005/0070929 | A1 | 3/2005 | Dalessandro et al. |
| 2005/0216055 | A1 | 9/2005 | Scirica et al. |
| 2012/0289979 | A1 | 11/2012 | Eskaros et al. |
| 2013/0068818 | A1 | 3/2013 | Kasvikis |
| 2013/0334280 | A1 | 12/2013 | Krehel et al. |
| 2014/0166723 | A1 | 6/2014 | Beardsly et al. |
| 2014/0239036 | A1 | 8/2014 | Zerkle et al. |
| 2014/0239037 | A1 | 8/2014 | Boudreaux et al. |
| 2014/0239038 | A1 | 8/2014 | Leimbach et al. |
| 2014/0239041 | A1 | 8/2014 | Zerkle |
| 2014/0239043 | A1 | 8/2014 | Simms et al. |
| 2014/0239044 | A1 | 8/2014 | Hoffman |
| 2015/0173752 | A1 | 6/2015 | Demmy et al. |
| 2015/0272575 | A1 | 10/2015 | Leimbach et al. |
| 2015/0282809 | A1 | 10/2015 | Shelton, IV et al. |
| 2016/0143659 | A1 | 5/2016 | Glutz et al. |
| 2016/0278774 | A1 | 9/2016 | Shelton, IV et al. |
| 2017/0055981 | A1 | 3/2017 | Vendely et al. |
| 2017/0056018 | A1* | 3/2017 | Zeiner .................. A61B 17/105 |
| 2017/0086823 | A1 | 3/2017 | Leimbach et al. |
| 2018/0235609 | A1 | 8/2018 | Harris et al. |
| 2018/0235610 | A1 | 8/2018 | Harris et al. |
| 2018/0235611 | A1 | 8/2018 | Harris et al. |
| 2018/0235619 | A1 | 8/2018 | Harris et al. |
| 2018/0325514 | A1 | 11/2018 | Harris et al. |
| 2018/0325515 | A1 | 11/2018 | Harris et al. |
| 2018/0325516 | A1 | 11/2018 | Harris et al. |
| 2019/0000481 | A1* | 1/2019 | Harris .............. A61B 17/07292 |
| 2019/0076143 | A1 | 3/2019 | Smith et al. |
| 2019/0175173 | A1* | 6/2019 | Harris ................ A61B 17/0686 |

FOREIGN PATENT DOCUMENTS

| | | |
|---|---|---|
| WO | WO 2013/151888 A1 | 10/2013 |
| WO | WO 2017/083129 | 5/2017 |

OTHER PUBLICATIONS

International Search Report and Written Opinion dated Apr. 19, 2018 for International Application No. PCT/US2018/017751, 17 pages.
U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
U.S. Appl. No. 16/035,872, filed Jul. 16, 2018.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
European Search Report, Partial, and Written Opinion dated Dec. 9, 2019 for Application No. EP 19186224.2, 11 pgs.
European Search Report, Extended, and Written Opinion dated Dec. 10, 2019 for Applicafion No. EP 19186231.7, 7 pgs.
European Search Report, Partial, and Provisional Written Opinion dated Oct. 31, 2019 for Application No. EP 119186252.3, 16 pgs.
European Search Report, Extended, and Written Opinion dated Jan. 31, 2020 for Application No. EP 119186252.3, 14 pgs.
International Search Report and Written Opinion dated Dec. 6, 2019 for Application No. PCT/IB2019/055980, 13 pgs.
International Search Report and Written Opinion dated Feb. 27, 2020 for Application No. PCT/IB2019/055983, 20 pgs.
Declaration of Non-Establishment of International Search Report and Written Opinion dated Dec. 13, 2019 for Application PCT/IB2019/055984, 6 pgs.
European Search Report and Written Opinion dated Nov. 12, 2019 for Application No. 19186244.0, 7 pgs.
International Search Report and Written Opinion dated Jan. 2, 2020 for Application No. PCT/IB2019/056041, 11 pgs.

* cited by examiner

BUTTRESS APPLIER CARTRIDGE FOR SURGICAL STAPLER HAVING END EFFECTOR WITH DEFLECTABLE CURVED TIP

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
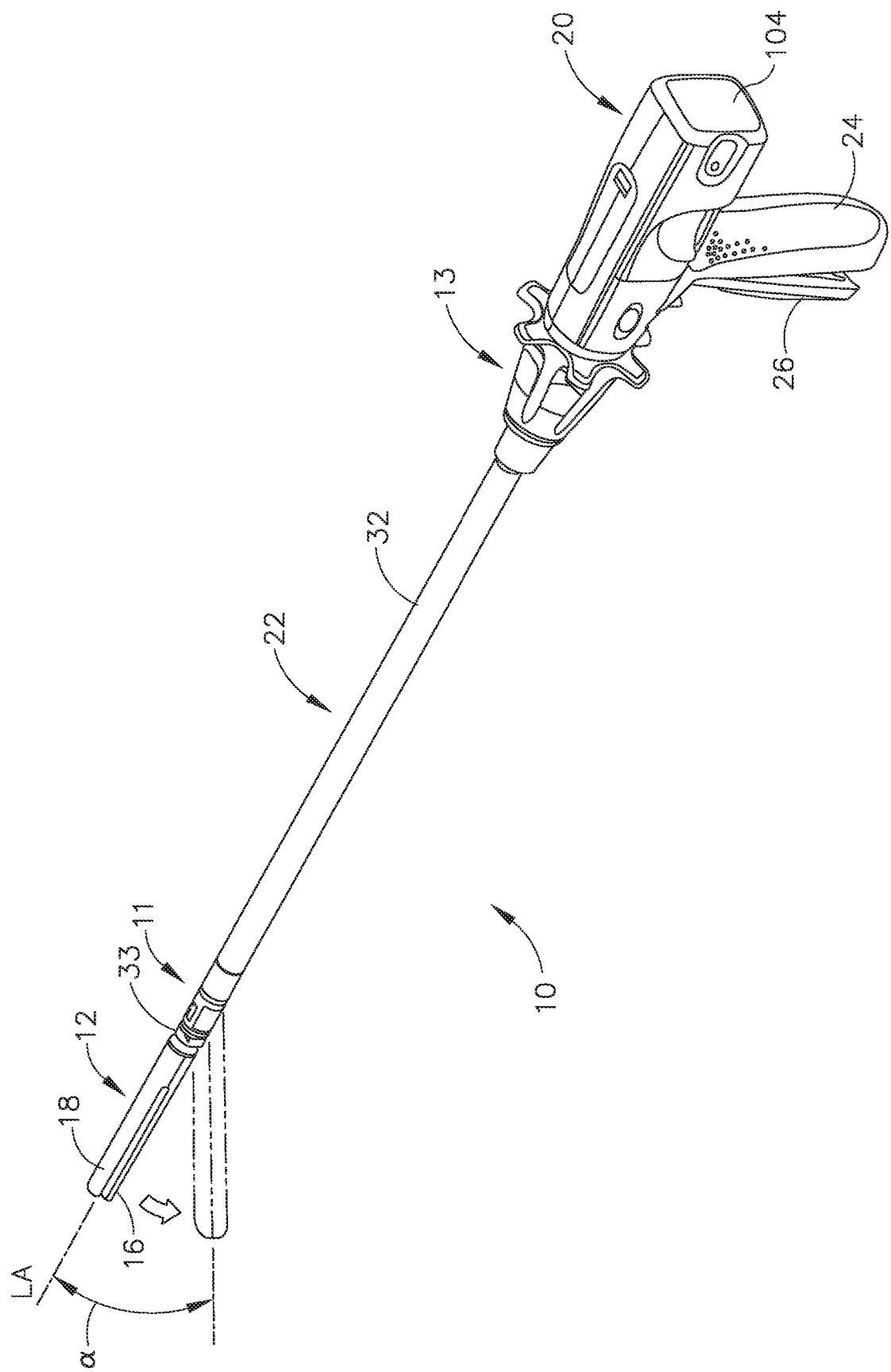
FIG. 1 depicts a perspective view of a first exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Surgical Instrument Having a First Exemplary End Effector

FIGS. 1-7 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
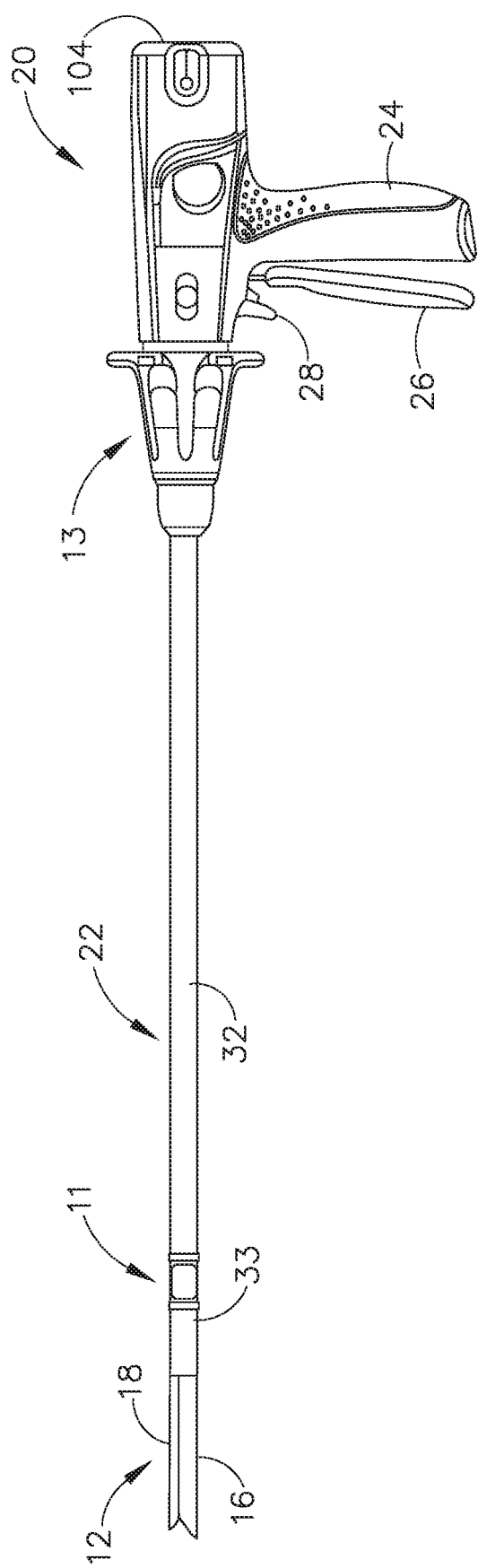
FIG. 2 depicts a side view of the instrument of FIG. 1 with a first exemplary end effector.

Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
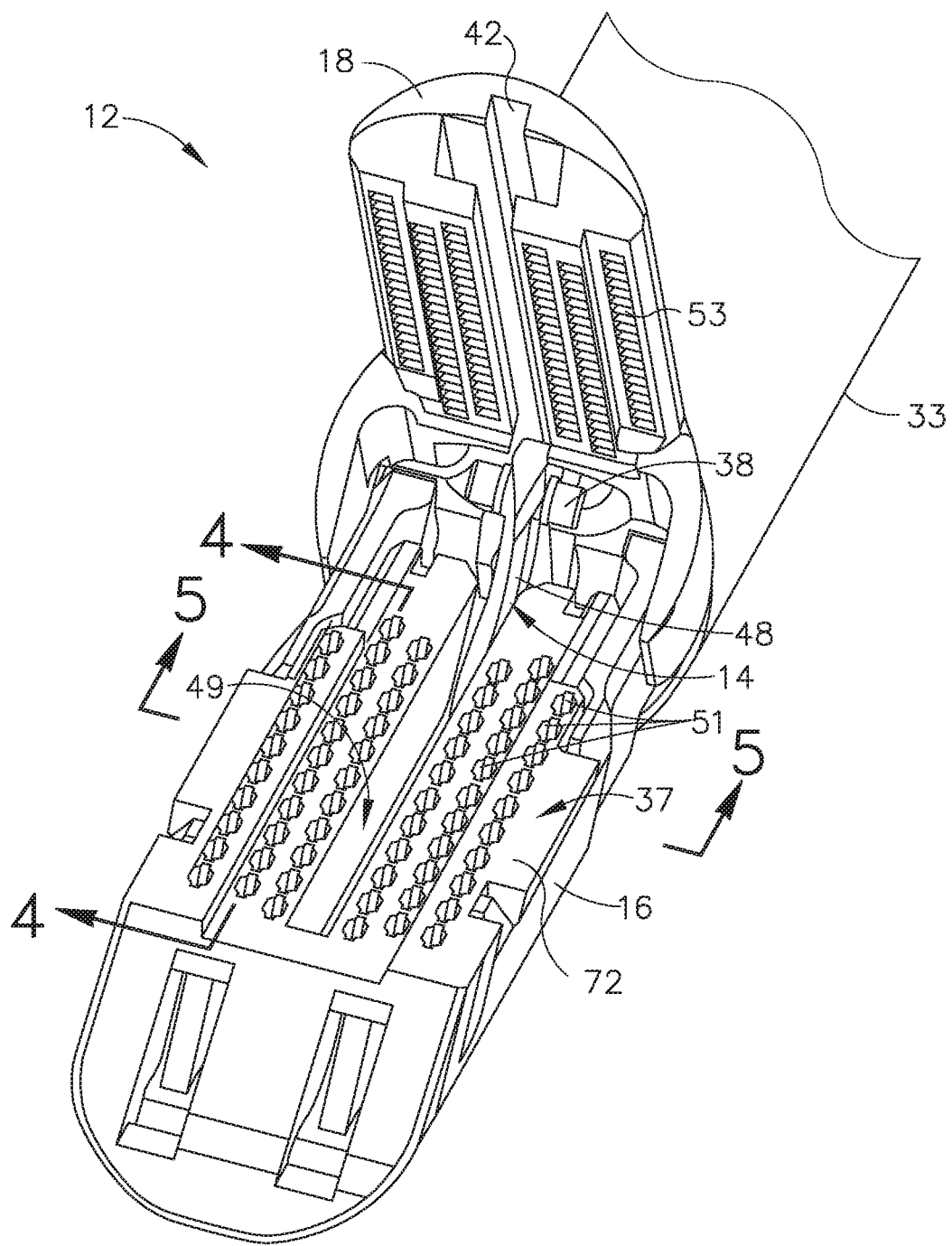
FIG. 3 depicts a perspective view of the end effector of the instrument of FIG. 1 in an open configuration.
Figure 4A:
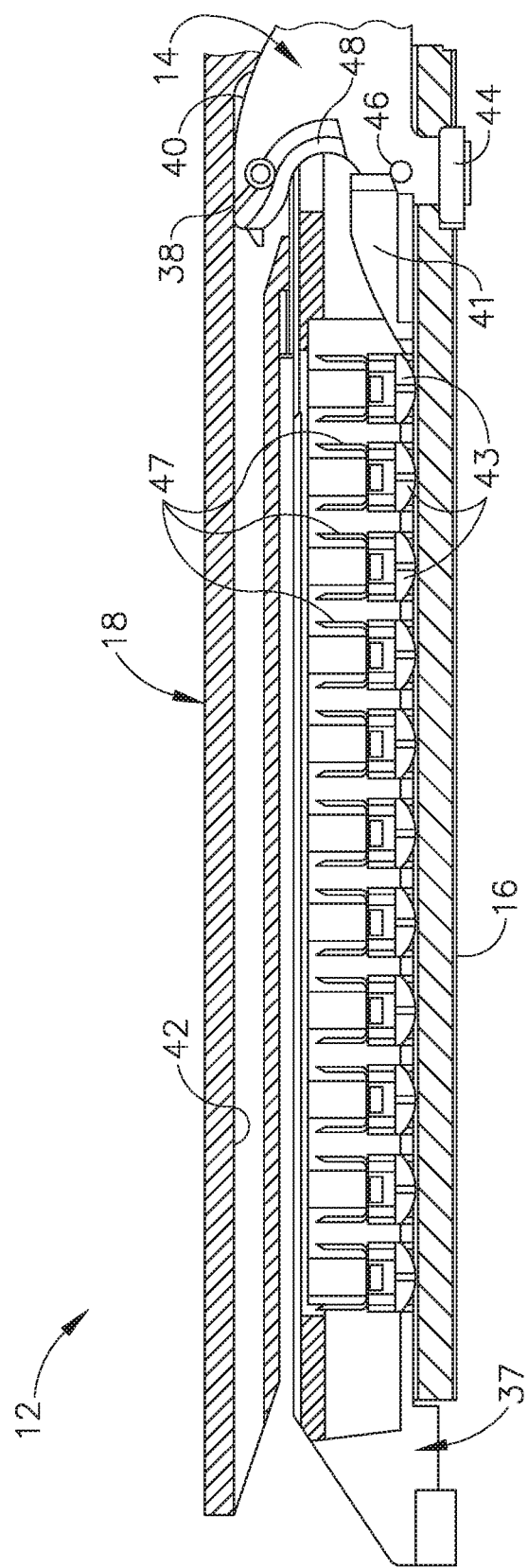
FIG. 4A depicts a side cross-sectional view of the end effector of FIG. 3, taken along line 4-4 of FIG. 3, with the firing beam in a proximal position.
Figure 4B:
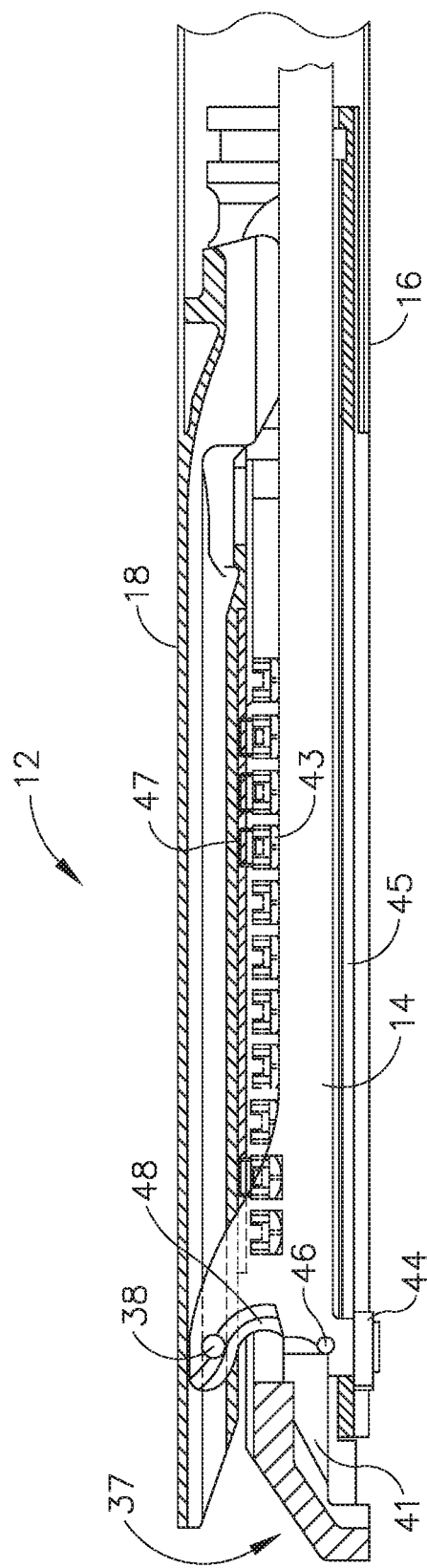
FIG. 4B depicts a side cross-sectional view of the end effector of FIG. 3, taken along line 4-4 of FIG. 3, with the firing beam in a distal position.
Figure 5:
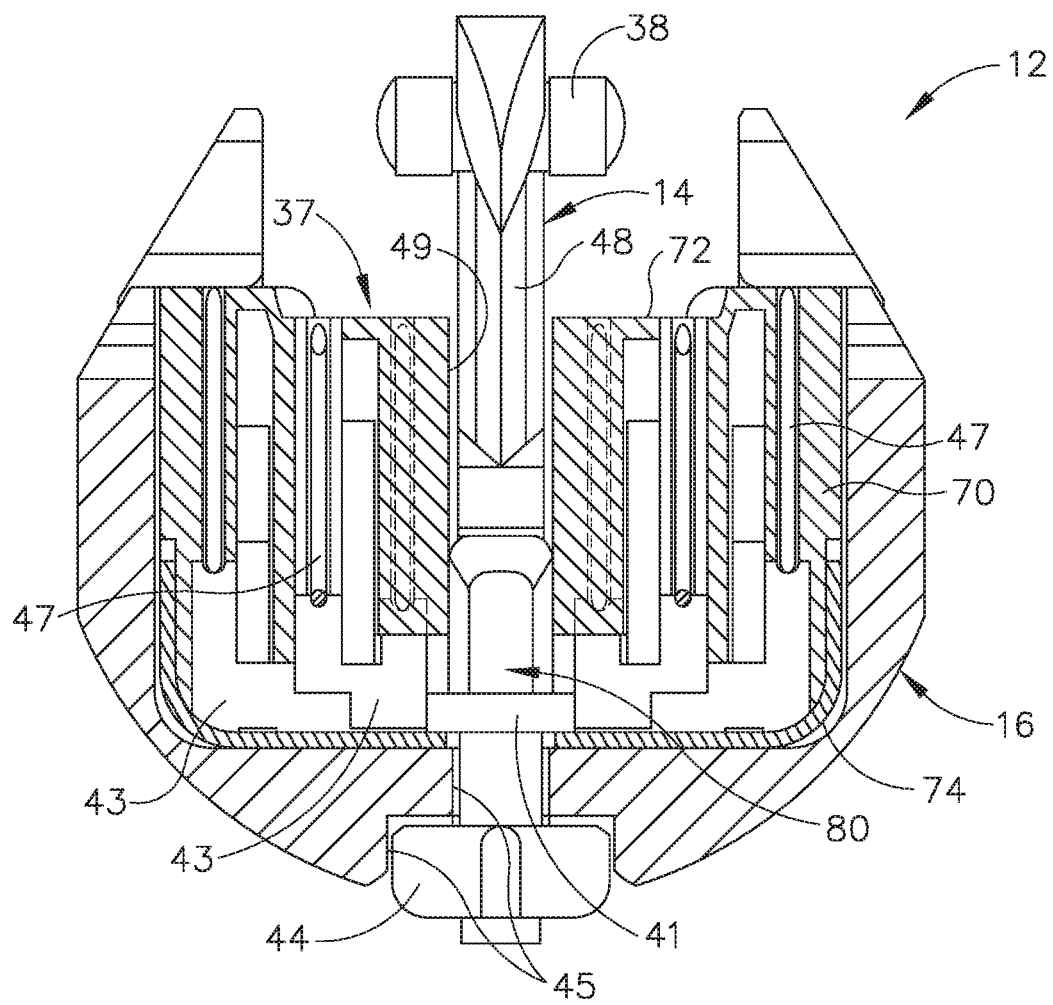
FIG. 5 depicts an end cross-sectional view of the end effector of FIG. 3, taken along line 5-5 of FIG. 3.
Figure 6:
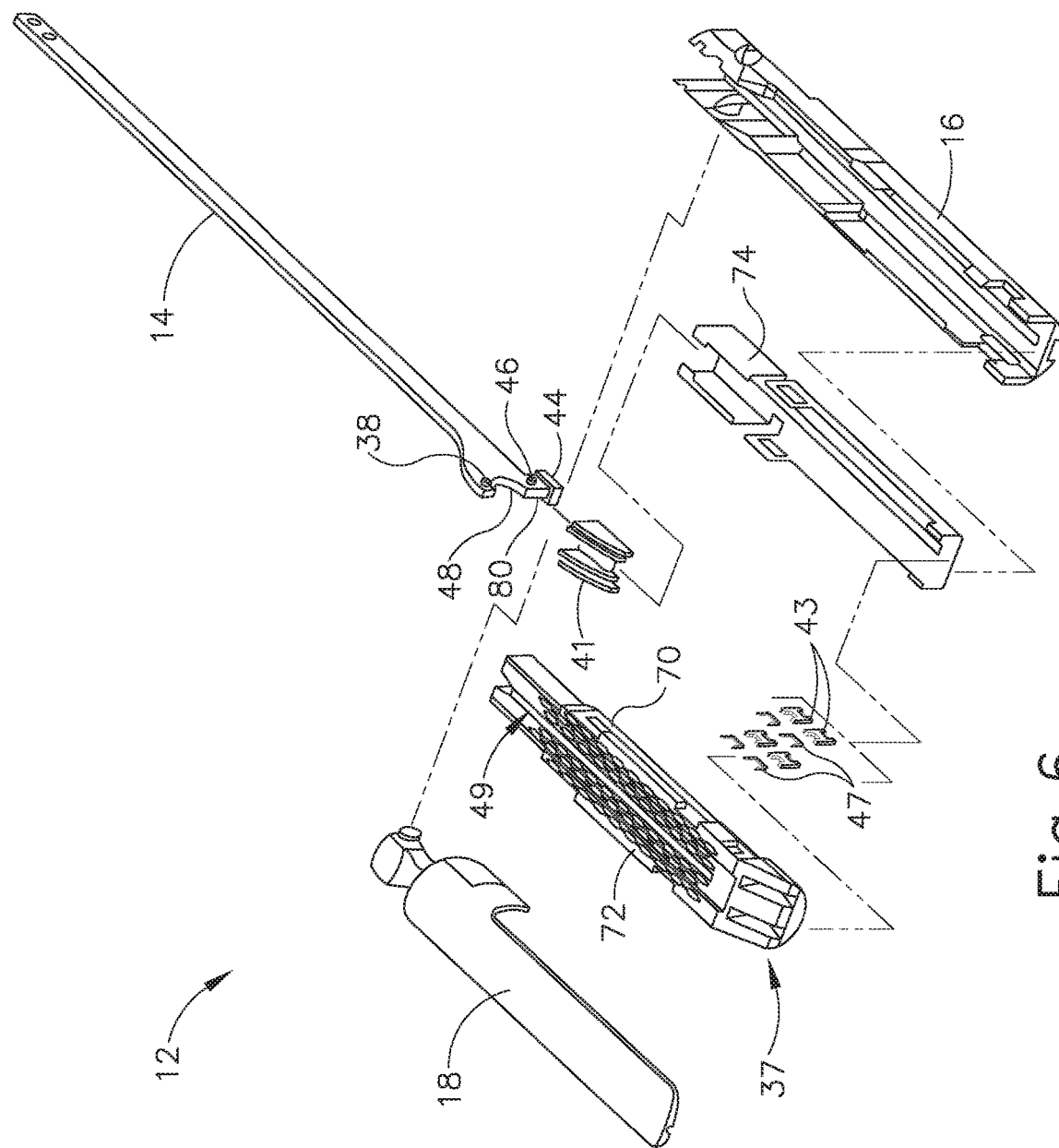
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5.

Figure 7:
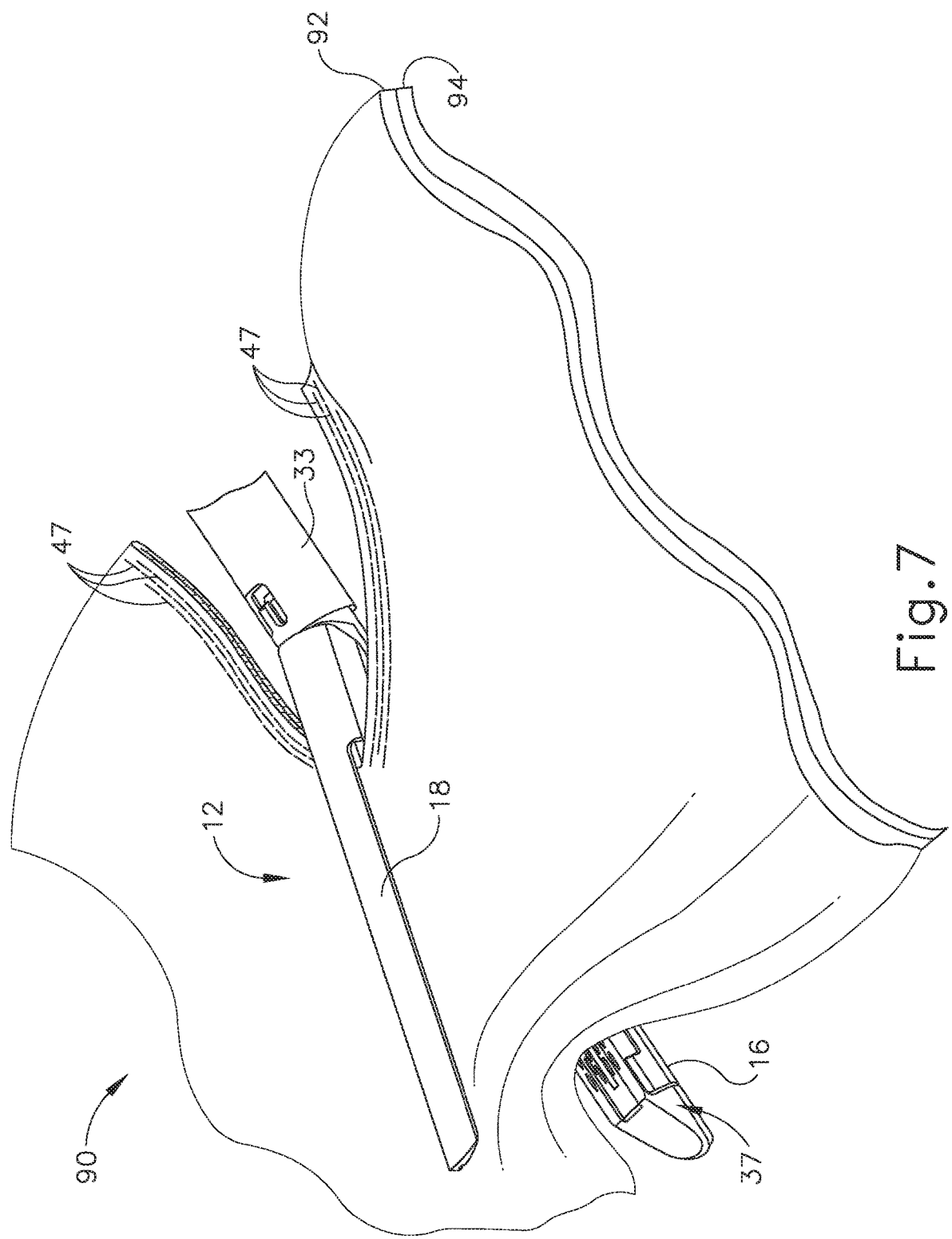
FIG. 7 depicts a perspective view of the end effector of FIG. 3, positioned at tissue and having been actuated once in the tissue.

FIG. 7 shows end effector (12) having been actuated through a single stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). End effector (12) is withdrawn from the patient after the first stroke is complete, spent staple cartridge (37) is replaced with a new staple cartridge, and end effector (12) is then again inserted to reach the stapling site for further cutting and stapling. This process may be repeated until the desired number of cuts and staples (47) have been provided.

Some versions of instrument (10) provide motorized control of firing beam (14).

Such motorized control may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein; and/or U.S. Pat. No. 8,210,411, entitled "Motor-Driven Surgical Instrument," issued Jul. 3, 2012, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition, or in the alternative, the pivot axis may slide along the slot/channel first, with anvil (18) then pivoting about the pivot axis after the pivot axis has slid a certain distance along the slot/channel. Such sliding/translating pivotal movement is encompassed within terms such as "pivot," "pivots," "pivotal," "pivotable," "pivoting," and the like.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. First Exemplary Surgical Instrument Having a Second Exemplary End Effector

As end effector (12) is inserted into a surgical site, the user may rotate shaft (22) and end effector (12) of instrument (10) during the procedure. In some instances, lower jaw (16) of end effector (12) is visible rather than anvil (18); while in other instances anvil (18) is visible rather than lower jaw (16). It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely encompass the vessel to be cut, such that the vessel may be fully cut and stapled in one single actuation. It may be desirable to enable the operator to more easily visually confirm proper position of anvil (18) and lower jaw (16) in relation to a vessel to fully clamp the vessel. One potential way of enhancing visualization of the surgical site may include improving visualization of the area adjacent to the distal tip of lower jaw (16) and anvil (18). It may also be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
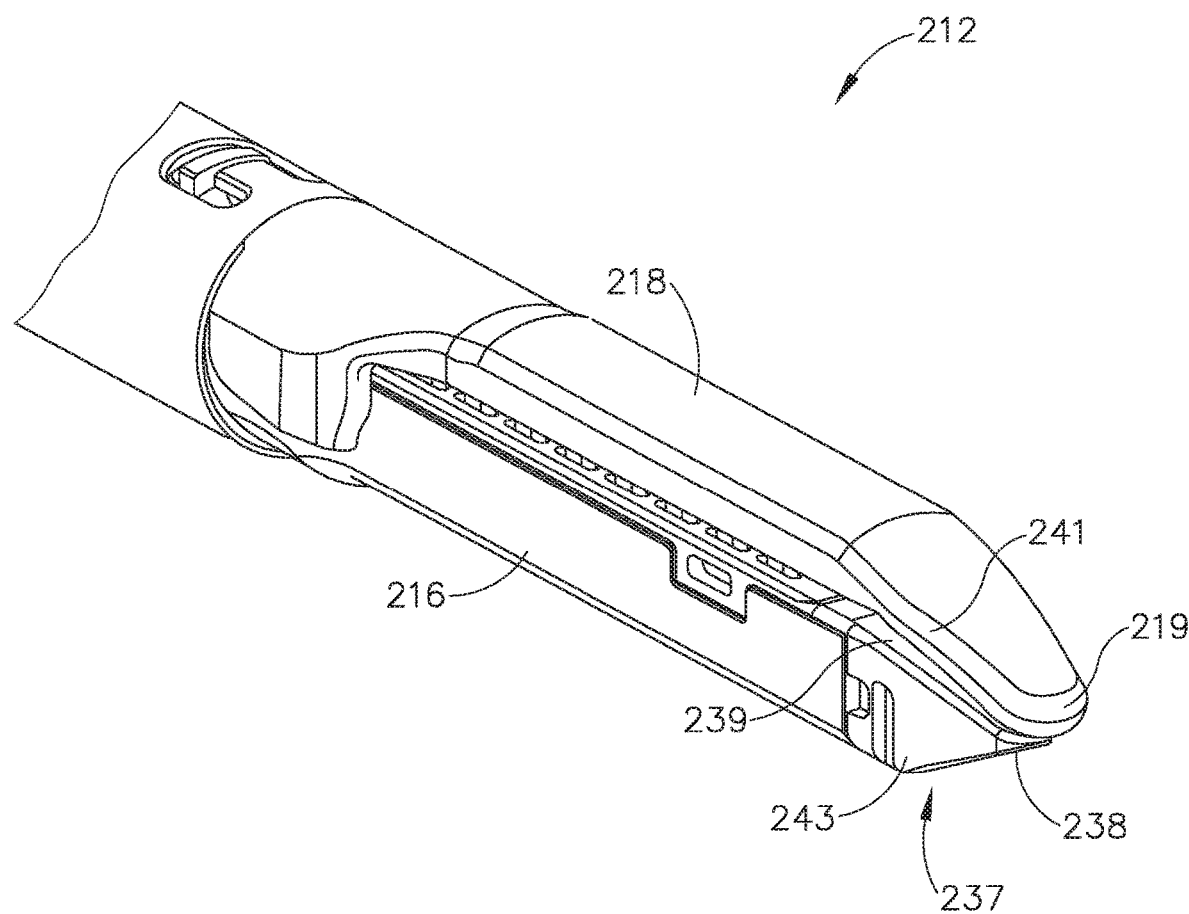
FIG. 8 depicts a perspective view of a second exemplary end effector that includes an angled cartridge and an angled anvil with a tip.

FIG. 8 depicts a second exemplary end effector (212) comprising an anvil (218) and a lower jaw (216). End effector (212) may be used in place of end effector (12) of instrument (10). End effector (212) may be integrally formed with instrument (10) or, in the alternative, may be interchangeable with end effector (12) of instrument (10). Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
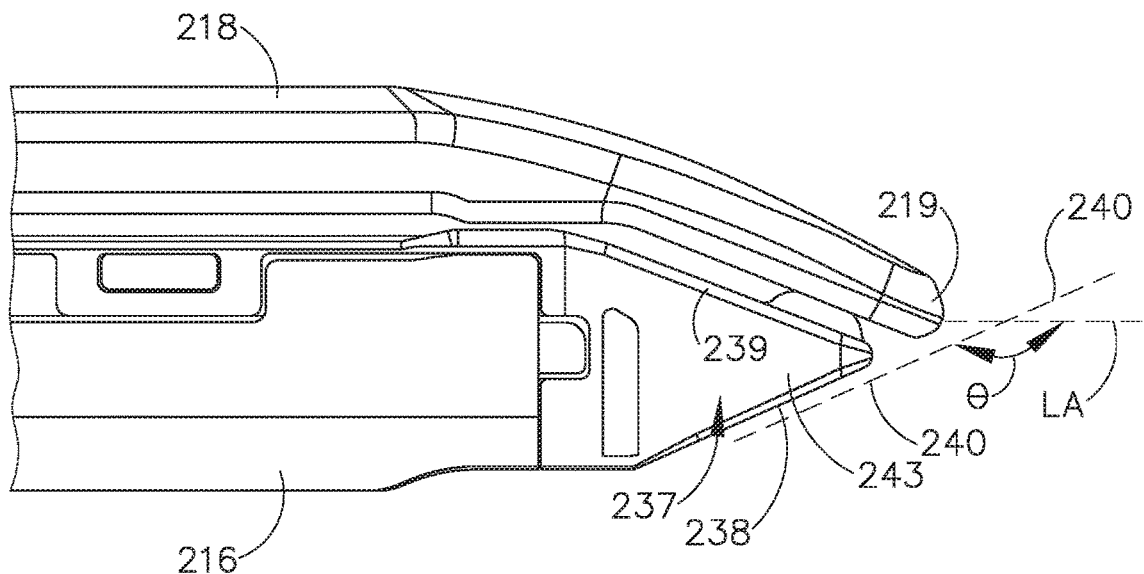
FIG. 9 depicts an enlarged side view of the end effector of FIG. 8.
Figure 10:
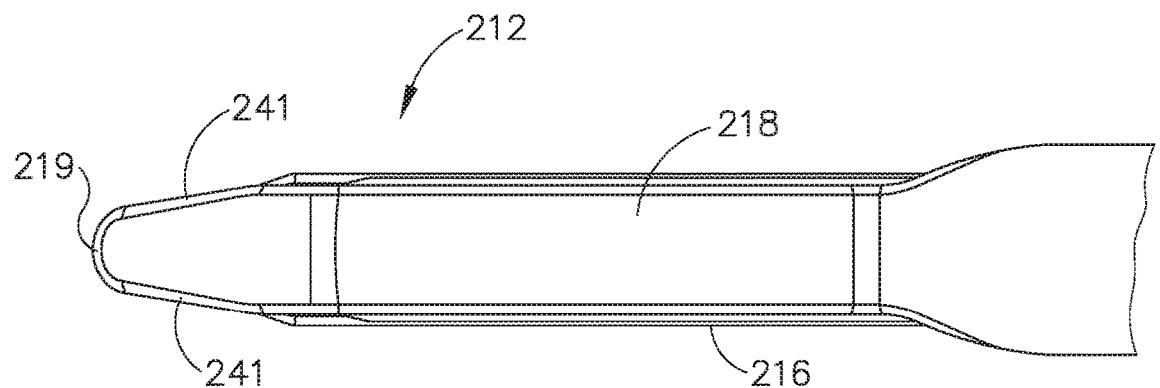
FIG. 10 depicts an enlarged top view of the end effector of FIG. 8.

Anvil (218) as shown in FIGS. 8-10 has an elongated shape where the distal portion of anvil (218) angles toward cartridge (237) such that the distal most tip (219) of anvil (218) extends distally longitudinally further than cartridge (237). Alternatively, distal most tip (219) may extend to a distance longitudinally equal to cartridge (237) or proximal relative to the distal most point on cartridge (237). As seen best in FIG. 10, anvil (218) includes sides (241) that taper laterally as they approach the distal most tip (219) of anvil (218). The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site.

Cartridge (237) is operable to hold staples like staples (47) shown in FIG. 4A for driving into tissue. As shown in FIG. 9, the distal end of cartridge (237) has a triangular profile defined by an upper tapered surface (239) and a lower tapered surface (238). The distal end of cartridge (237) also comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). Sight line (240) intersects longitudinal axis (LA), which extends longitudinally through end effector (212), to form a viewing angle (θ).

The planar shape of lower tapered surface (238) facilitate visualization of the distal most tip (219) of anvil (218). Viewing angle (θ) may establish the relative visibility that a user has of distal most tip (219), such that the user can see in front of distal most tip (219) along any line of sight that passes through the intersection of sight line (240) and longitudinal axis (LA) within viewing angle (θ). As viewing angle (θ) increases, the user would have greater visibility of the area immediately in front of distal most tip (219) from proximal vantage points; whereas as viewing angle (θ) decreases, the user has less visibility of the area in front of distal most tip (219) from proximal vantage points. In some versions, viewing angle (θ) defines an angle greater than 90 degrees. Additionally, in some versions, viewing angle (θ) defines an angle greater than 135 degrees. In the illustrated version, the user generally looks along sight line (240) or along some other line of sight within viewing angle (θ), such that the user has visibility along sight line as well as any area within viewing angle (θ). The underside of distal most tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). In some instances, end effector (212) may be rotated before, during, or after clamping tissue (90). As a result, the tapered shape of anvil (218) may also provide more accessible viewing of distal most tip (219) or substantially adjacent distal most tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). Lower tapered surface (238) and the tapered shape of anvil (218) may provide a lead-in, guiding the rest of end effector (212) into the trocar. Visibility and maneuverability may thus be enhanced by the tapered design for both sides (241) of anvil (218) and each side (243) of cartridge (237).

In addition to the foregoing, end effector (212) and versions of instrument (10) incorporating end effector (212) may be configured and operable in accordance the teachings of any one or more of the patent references cited herein. Further modifications that may be incorporated into end effector (212) will be described in greater detail below.

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then be removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages, such as enhanced visualization, maneuverability, and/or tissue-gathering effects. However, in versions where all the structures of end effector (212) are rigid, the bent configuration of distal most tip (219) of anvil (218) may not lend itself well to marching operations, as distal most tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all the tissue that is to be cut and stapled is gathered proximal to distal most tip (219).

In view of the foregoing, it may be desirable to provide a variation of end effectors (12, 212) that provides the marching capabilities of end effector (12), the improved visibility, maneuverability, and tissue-gathering effects associated with end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. Providing a deformable tip can provide an additional level of maneuverability benefits in terms of navigating through tissue to a surgical site. In this manner, the deformable tip may deflect or deform to promote smooth and atraumatic movement of the end effector through tissue, particularly during marching operations.

Figure 11:
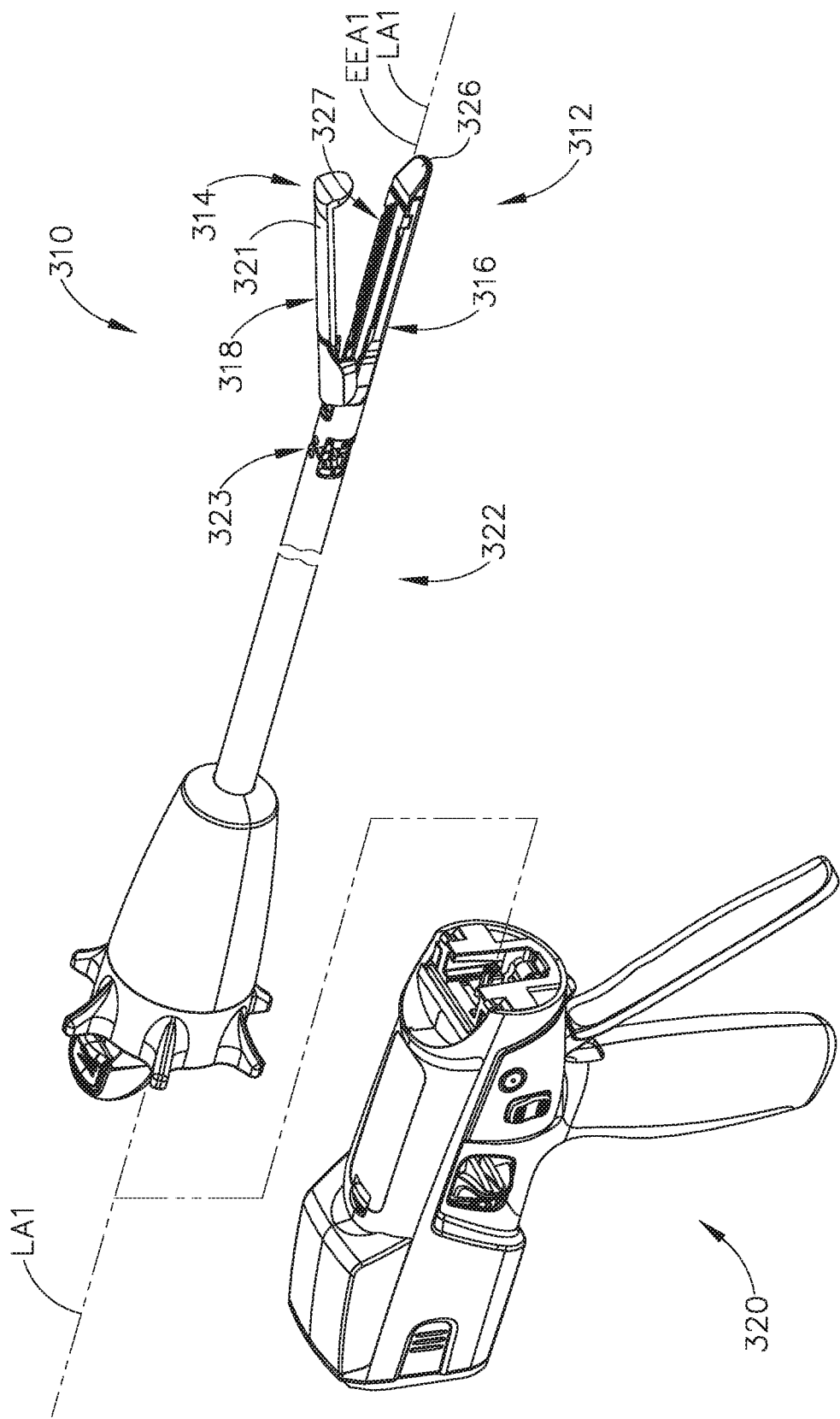
FIG. 11 depicts a perspective view of a second surgical stapling instrument with a third end effector with a first placement tip, where the upper and lower jaws are in an open configuration.

III. Second Exemplary Surgical Instrument Including End Effector with Placement Tip FIG. 11 show a second exemplary instrument (310) with exemplary end effector (312) and exemplary placement tip (314). Instrument (310) may have a modular configuration such that shaft (322) is selectively removable from, and selectively attachable to, handle portion (320). Instrument (310) is configured similarly to instrument (10), such that the operability and use of instrument (310) is the same as described above for instrument (10) with the added feature of instrument (310) having a modular configuration. With its modular configuration, instrument (310) provides a way to change the desired end effector. Features operable for providing the modular configuration of instrument (310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

End effector (312) is provided on shaft (322) that is detachable from handle portion (320). End effector (312) is operable to compress, staple, and cut tissue. End effector (312) may be used in place of end effector (12) shown in FIG. 1. In some versions, end effector (312) may be integrally formed with shaft (322) or, alternatively, may be separately formed and subsequently combined. In some versions, end effector (312) may be provided for use in robotic systems. In such robotic systems, modular shaft (322) having any of the following end effector (312) may be attachable to a portion of the robotic system for use such that handle portion (320) is replaced by components of the robotic system, including a body. Other ways to incorporate end effector (312) having any of the following placement tips (314) into a user operated or robotic operated instrument will be apparent to those of ordinary skill in the art.

Placement tip (314) is operable to elastically deform from a non-deflected position to a deflected position. Placement tip (314) obtains the non-deflected position when end effector (312) is not clamping tissue. More specifically, in this non-deflected position, end effector (312) may be in the open configuration as shown in FIG. 11, or in the closed configuration as shown in FIGS. 8 and 9 with respect to end effector (212). In instances when end effector (312) are in this non-deflected position, end effector (312) may be considered in a non-loaded state or non-loaded position. Conversely, in the deflected position (not shown) when end effector (312) is clamping tissue, end effector (312) may be considered in a loaded state or a loaded position. In the deflected position, at least a portion of placement tip (314) deflect upwardly. The deflected position for placement tip (314) may be substantially straight in some versions, but may be deflected to a degree (e.g., slightly above or slightly below longitudinal (LA1)) in other versions. It should be understood that the deflected position for placement tip (314) may be defined by the characteristics (e.g., thickness, density, etc.) of the tissue that is being captured between respective lower jaw (316) and anvil (318), thereby causing the deflection of placement tip (314). In some variations, placement tip (314) does not deflect in response to a load.

FIG. 11 shows surgical instrument (310), configured as a surgical stapler, that comprises a third exemplary end effector (312) and a first exemplary placement tip (314). End effector (312) includes an upper jaw and a lower jaw (316), with the upper jaw including an anvil (318). Instrument (310) additionally includes a body, shown as a handle portion (320), and a shaft (322) that extends from handle portion (320). As shown in FIG. 11, shaft (322) defines a longitudinal axis (LA1) that is colinear with an end effector axis (EEA1) of end effector (312), but which may non-colinear, and instead angled, when end effector (312) is articulated relative to shaft (322) using articulation joint (323).

Placement tip (314) is located adjacent at least one of a distal end (321) of anvil (318) or a distal end of lower jaw (316). As shown in FIG. 11, placement tip (314) is coupled with distal end (321) of anvil (318). Placement tip (314) may be permanently coupled with anvil (318), or alternatively, placement tip (314) may be removably coupled with anvil (318). Placement tip (314) may be integrally formed together with anvil (318) as unitary piece or consist of separately formed components. Placement tip (314) may be positioned on the same jaw as staple cartridge (324) or on the same jaw as anvil (318). As shown in FIG. 11, upper jaw includes anvil (318), while lower jaw (316) is removably coupled with staple cartridge (324). However, this relationship may be reversed if desired. Staple cartridge (324) is configured to hold one or more staples in a manner similar to staple cartridge (37). Staple cartridge includes an angled distal portion (326). As previously described, at least one of anvil (318) or lower jaw (316) is movable relative to other of anvil (318) or lower jaw (316) between the open configuration and the closed configuration. As shown, anvil (318) pivotably rotates toward lower jaw (316) in the same manner as anvil (18) as described above with respect to instrument (10). In this manner, end effector (312) is like end effector (12), except for the laterally deflected configuration and deformability of placement tip (314).

IV. Exemplary Buttress Assembly for Surgical Stapler

In some instances, it may be desirable to equip end effectors (12, 212, 312) with a buttress material to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18, 218, 318) that faces staple cartridge (37, 237, 324). It should also be understood that a first buttress may be provided on upper deck (72) of staple cartridge (37, 237, 324) while a second buttress is provided on anvil (18, 218, 318) of the same end effector (12, 212). Various examples of forms that a buttress may take will be described in greater detail below. Various ways in which a buttress may be secured to a staple cartridge (37, 237, 324) or an anvil (18, 218, 318) will also be described in greater detail below. Exemplary buttress assemblies, exemplary materials and techniques for applying buttress assemblies, and exemplary buttress applier cartridges may be configured in accordance with at least some of the teachings of U.S.AA U.S. Pub. No. 2017/0055981 entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein.

A. Exemplary Composition of Buttress Assembly for Surgical Stapler

Figure 12:
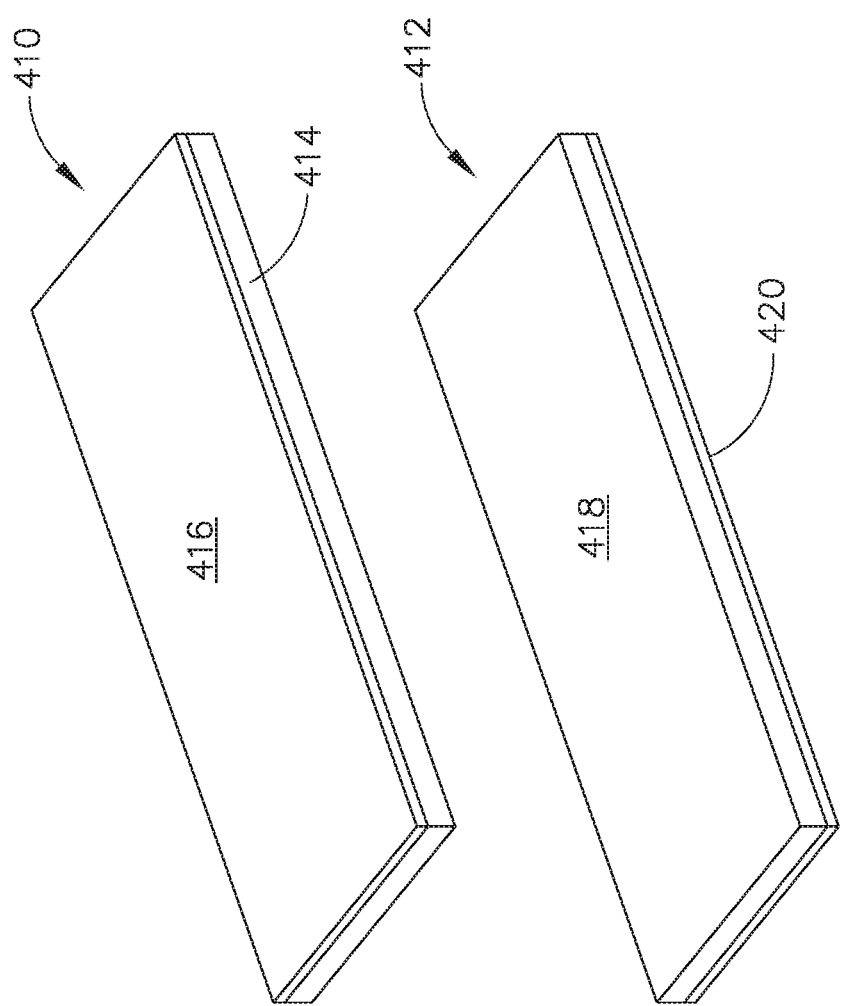
FIG. 12 depicts a perspective view of an exemplary upper buttress and an exemplary lower buttress of an exemplary buttress assembly, each of which may be applied to the end effector of FIG. 2 or the end effector of FIG. 8.

FIG. 12 shows an exemplary pair of buttress assemblies (410, 412) with a basic composition. Buttress assembly (410) of this example comprises a buttress body (414) and an upper adhesive layer (416). Similarly, buttress assembly (412) comprises a buttress body (418) and a lower adhesive layer (420). In the present example, each buttress body (414, 418) comprises a strong yet flexible material configured to structurally support a line of staples (447). By way of example only, each buttress body (414, 418) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (414, 418).

Each buttress body (414, 418) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (414, 418) may comprise other adjuncts or hemostatic agents such as thrombin may be used such that each buttress body (414, 418) may assist to coagulate blood and reduce the amount of bleeding at the surgical site. Other adjuncts or reagents that may be incorporated into each buttress body (414, 418) may further include but are not limited to medical fluid or matrix components. Merely illustrative examples of materials that may be used to form each buttress body (414, 418), as well as materials that may be otherwise incorporated into each buttress body (414, 418), are disclosed in U.S. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used.

In the present example, adhesive layer (416) is provided on buttress body (414) to adhere buttress body (414) to underside (424) of anvil (18). Similarly, adhesive layer (420) is provided on buttress body (418) to adhere buttress body (418) to upper deck (72) of staple cartridge (37). Such an adhesive material may provide proper positioning of buttress body (414, 418) before and during actuation of end effector (12); then allow buttress body (414, 418) to separate from end effector (12) after end effector (12) has been actuated, without causing damage to buttress body (414, 418) that is substantial enough to compromise the proper subsequent functioning of buttress body (414, 418). Examples of various suitable materials that may be used to form adhesive layers (416, 420) are disclosed in U.S. Pub. No. 2016/0278774, issued as U.S. Pat. No. 10,349,939 on Jul. 16, 2019, the disclosure of which is incorporated by reference herein.

Figure 13:
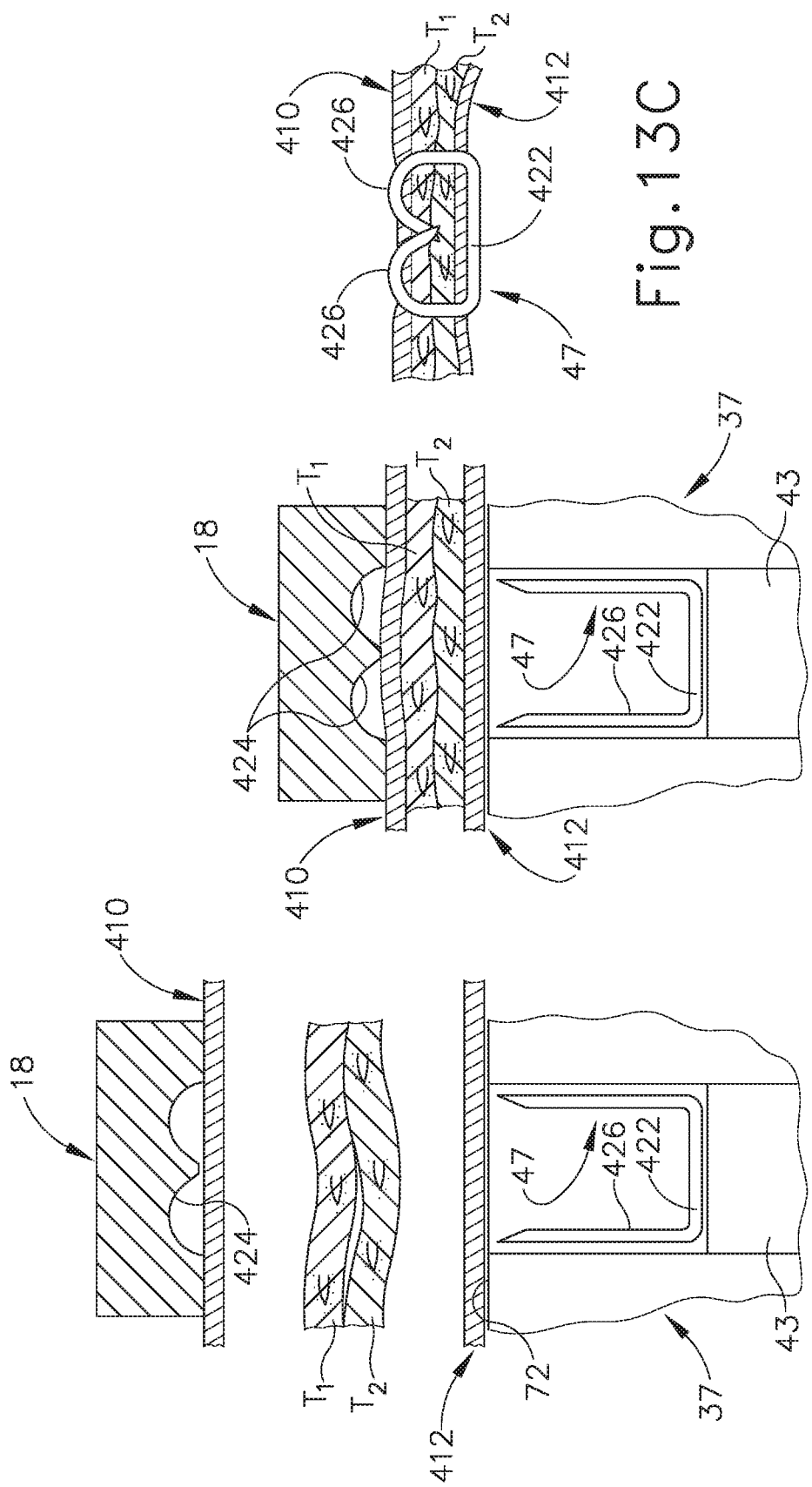
FIG. 13A depicts a cross-sectional end view of a portion of the end effector of FIG. 2 with a buttress assembly formed by the buttresses of FIG. 12 applied to the end effector, with tissue positioned between the buttresses in the end effector, and with the end effector in an open configuration.
FIG. 13B depicts a cross-sectional end view of the end effector and buttress assembly of FIG. 13A, with tissue positioned between the buttresses in the end effector, and with the end effector in a closed configuration.
FIG. 13C depicts a cross-sectional view of a staple and the buttress assembly of FIG. 13A having been secured to the tissue by the end effector of FIG. 2.

B. Exemplary Materials and Techniques for Providing Adhesion of Buttress to Surgical Stapler FIGS. 13A-13C show a sequence where an end effector (12) that has been loaded with buttress assemblies (410, 412) is actuated to drive staples (47) through two opposed layers of tissue ($T_1$, $T_2$), with buttress assemblies (410, 412) being secured to the same layers of tissue ($T_1$, $T_2$) by staples (47). In particular, FIG. 13A shows layers of tissue ($T_1$, $T_2$) positioned between anvil (18) and staple cartridge (37), with anvil (18) in the open position. Buttress assembly (410) is adhered to underside (424) of anvil (18) via adhesive layer (416); while buttress assembly (412) is adhered to upper deck (72) of staple cartridge (37) via adhesive layer (420). Layers of tissue ($T_1$, $T_2$) are thus interposed between buttress assemblies (410, 412). Next, closure trigger (26) is pivoted toward pistol grip (24) to drive closure tube (32) and closure ring (33) distally. This drives anvil (18) to the closed position as shown in FIG. 13B. At this stage, layers of tissue ($T_1$, $T_2$) are compressed between anvil (18) and staple cartridge (37), with buttress assemblies (410, 412) engaging opposite surfaces of tissue layers ($T_1$, $T_2$). End effector (12) is then actuated as described above, driving staple (47) through buttress assemblies (410, 412) and tissue ($T_1$, $T_2$). As shown in FIG. 13C, crown (422) of driven staple (47) captures and retains buttress assembly (412) against layer of tissue ($T_2$). Deformed legs (426) of staple (47) capture and retain buttress assembly (410) against layer of tissue ($T_1$).

Figure 14:
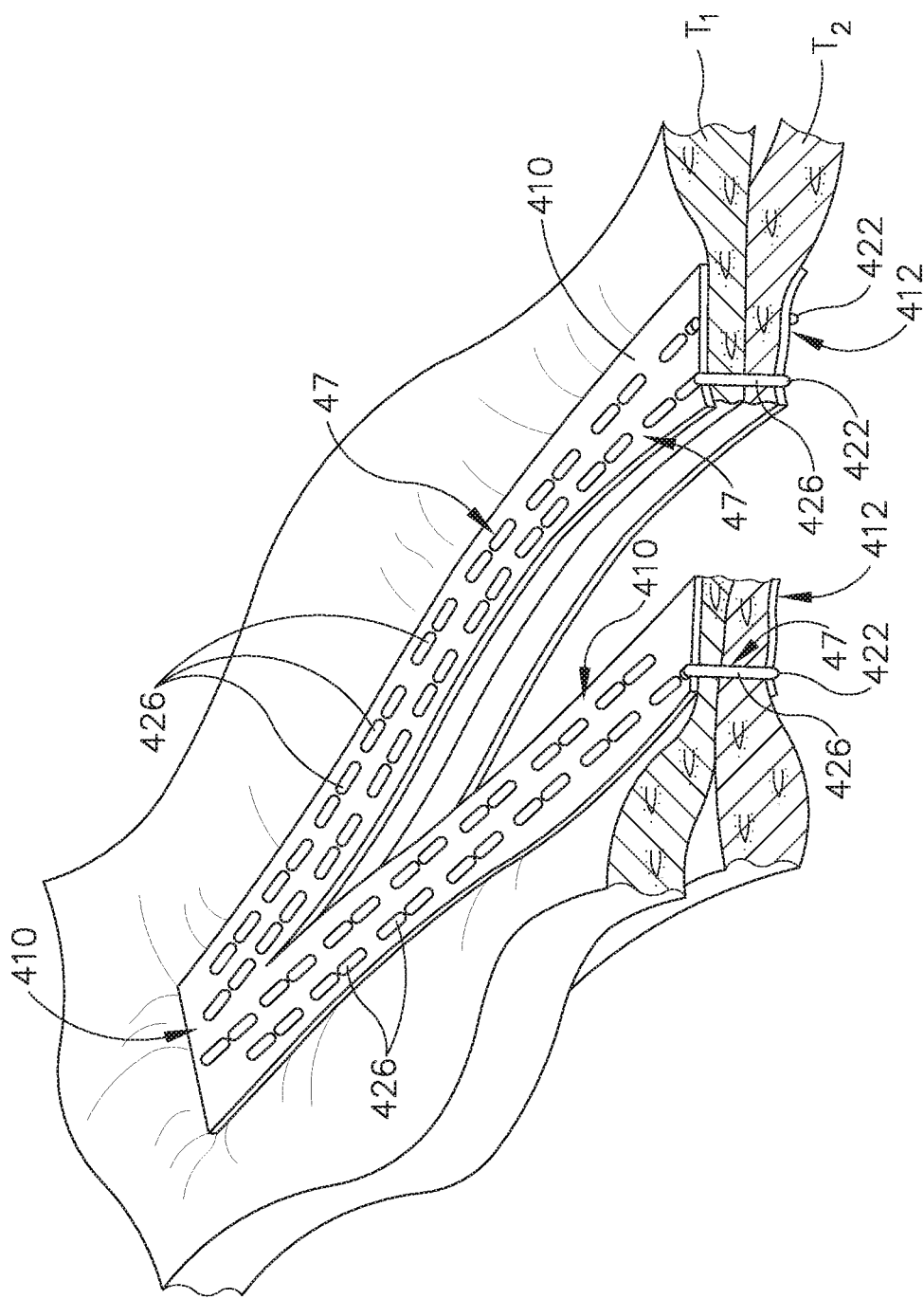
FIG. 14 depicts a perspective view of staples and the buttress assembly of FIG. 13A having been secured to the tissue by the end effector of FIG. 2.

A series of staples (47) will similarly capture and retain buttress assemblies (410, 412) against layers of tissue ($T_1$, $T_2$), thereby securing buttress assemblies (410, 412) to tissue ($T_1$, $T_2$) as shown in FIG. 14. As end effector (12) is pulled away from tissue ($T_1$, $T_2$) after deploying staples (47) and buttress assemblies (410, 412), buttress assemblies (410, 412) disengage end effector), such that buttress assemblies (410, 412) remain secured to tissue ($T_1$, $T_2$) with staples (47). Buttress tissue ($T_1$, $T_2$) thus provide structural reinforcement to the lines of staples (47). As can also be seen in FIG. 14, distally presented cutting edge (48) of firing beam (14) also cuts through a centerline of buttress tissue assemblies (410, 412), separating each buttress assemblies (410, 412) into a corresponding pair of sections, such that each section remains secured to a respective severed region of tissue ($T_1$, $T_2$).

C. First Exemplary Buttress Applier Cartridge with Active Retainer Arms

Figure 15:
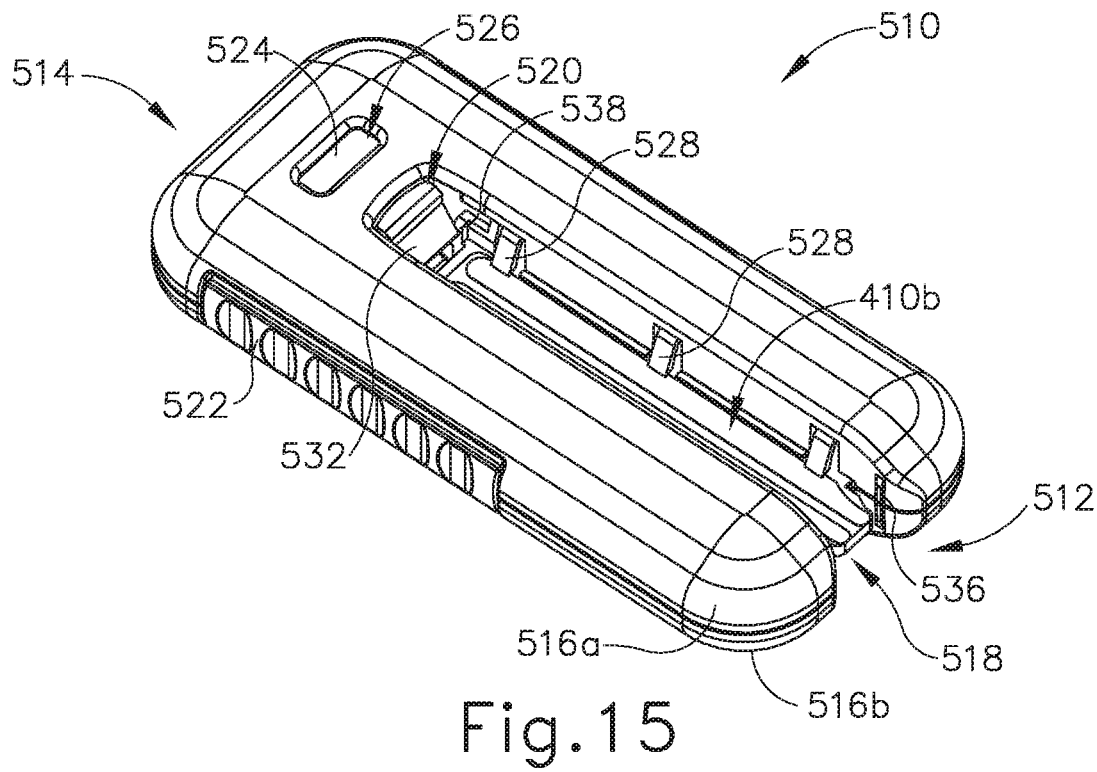
FIG. 15 depicts a perspective view of a first exemplary buttress applier cartridge that may be used to carry and apply the buttress assembly of FIG. 12.
Figure 16:
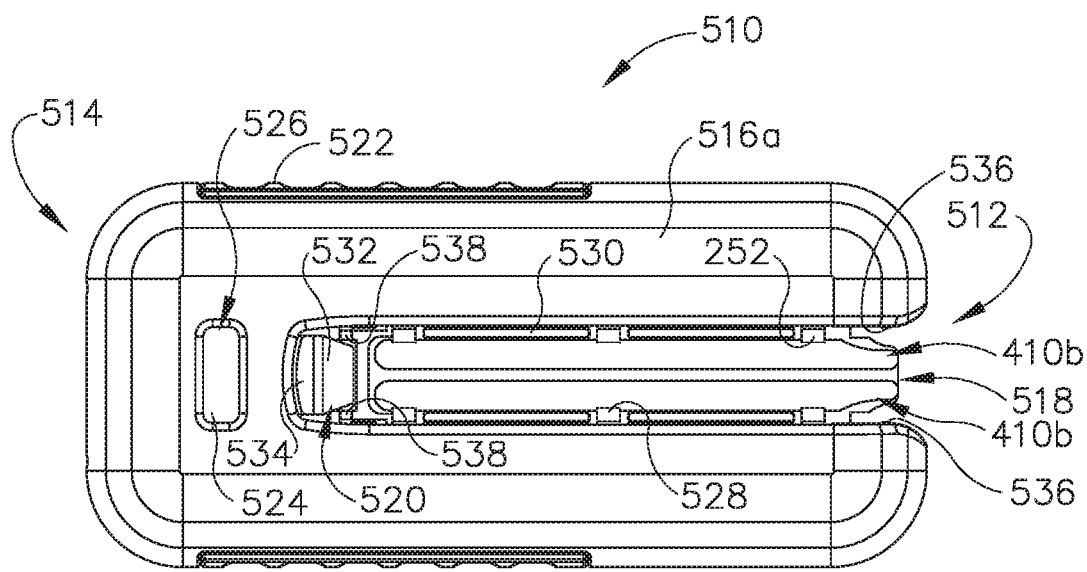
FIG. 16 depicts a top plan view of the buttress applier cartridge of FIG. 15.

Because end effector (12) may be actuated many times during use of instrument (10) in a single surgical procedure, it may be desirable to enable an operator to repeatedly and easily load buttress assemblies (410) on underside (424) of anvil (18) during that single surgical procedure. FIGS. 15-17B show a first exemplary buttress applier cartridge (510) that may be used to support and protect buttress assemblies (410, 412). Cartridge (510) may also be used to easily load buttress assemblies (410, 412) on end effector (12). As best seen in FIGS. 15-16, cartridge (510) of this example comprises an open end (512) and a closed end (514). Open end (512) is configured to receive end effector (12) as will be described in greater detail below. Cartridge (510) further includes a first housing (516a) and a second housing (516b), which each generally define a "U" shape to present open end (512). A platform (518) and a sled retainer (520) are interposed between first and second housings (516a-b).

Platform (518) of the present example is configured to support a pair of buttress assemblies (410) on one side of platform (518) and another pair of buttress assemblies (412) on the other side of platform (518). Platform (518) is exposed in recesses that are formed between the prongs of the "U" configuration of first and second housings (516a-b). Each buttress assembly (410, 412) is provided in a respective pair of portions that are separated to avoid spanning across slots (42, 49) of anvil (18) and staple cartridge (37), respectively, though platform (518) may just as easily support wide versions of buttress assemblies (410, 412) that unitarily span across slots (42, 49) of anvil (18) and staple cartridge (37), respectively. More specifically, the outer edges of platform (518) include retention features (530) in the form of ridges that further engage first and second housings (516a-b) to prevent platform (518) from sliding relative to first and second housings (516a-b).

First and second housings (516a-b) include integral gripping features (522) that have a surface geometry that is configured to promote an operator's grip of cartridge (510) during use of cartridge (510). Indicator plates (524) are positioned to correspond with windows (526) that are formed in first and second housings (516a-b), such that indicator plates (524) are visible through windows (526) at different times. Arms (528) of the present example are configured to selectively secure buttress assemblies (410, 412) to platform (518). In the present example, arms (528) are resilient and are thus configured to resiliently bear against buttress assemblies (410, 412), thereby pinching buttress assemblies (410, 412) against platform (518). Buttress applier cartridge (510) includes a tapered cam surface (532) and a housing engagement feature (534). As best seen in FIG. 16, housing engagement features (534) are positioned to engage corresponding surfaces of first and second housings (516a-b). As shown in FIGS. 15-16, first and second housings (516a-b) include proximal guide features (536) and distal guide features (538). Guide features (536, 538) are configured to assist in providing proper alignment of end effector (40) with cartridge (510). In the present example, guide features (536, 538) are unitarily formed features of first and second housings (516a-b).

Figure 17A:
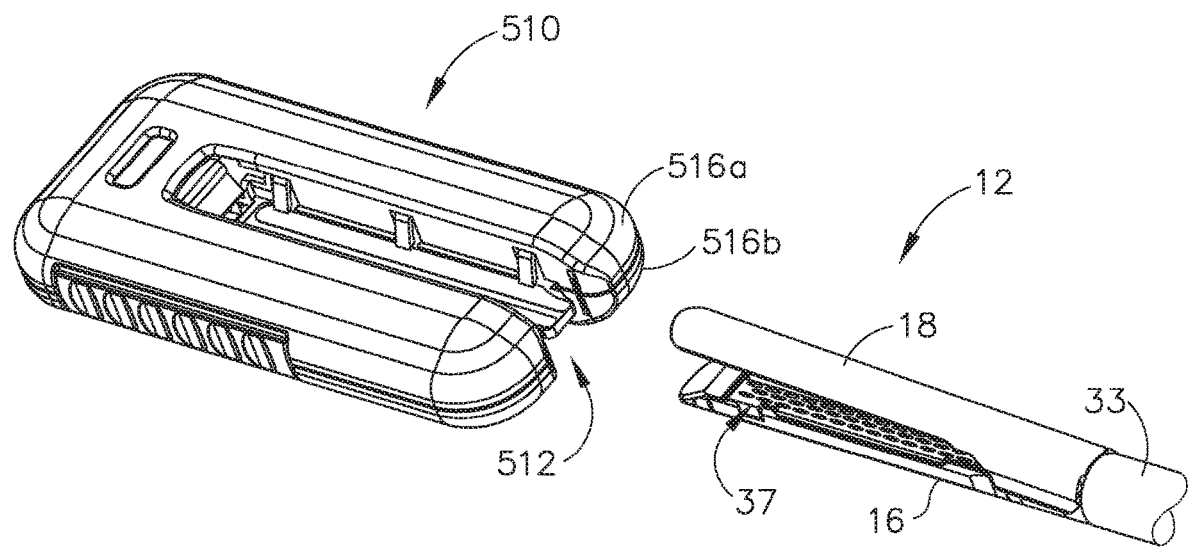
FIG. 17A depicts a perspective view of the end effector of FIG. 2 and the buttress applier cartridge of FIG. 15, with the end effector approaching the buttress applier cartridge.
Figure 17B:
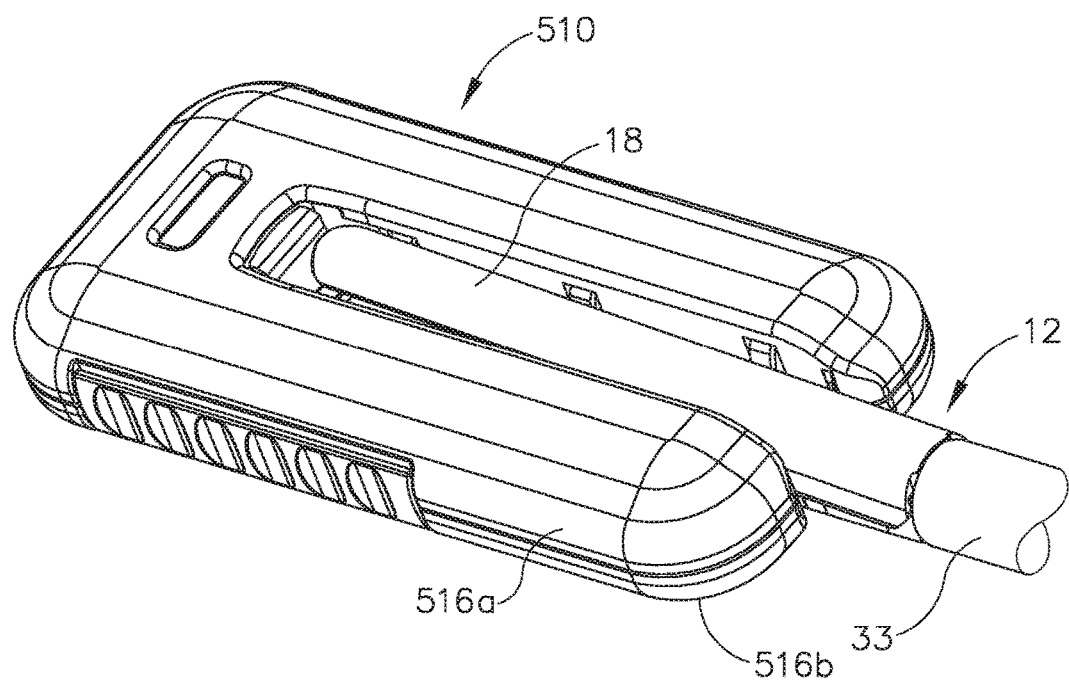
FIG. 17B depicts a perspective view of the end effector of FIG. 2 and the buttress applier cartridge of FIG. 15, with the buttress applier cartridge positioned in the end effector.

FIG. 17A shows cartridge (510) in a configuration where retainer arms (528) are positioned to hold buttress assemblies (410, 412) against platform (518); while FIG. 17B shows cartridge (510) in a configuration where retainer arms (528) are positioned to release buttress assemblies (410, 412) from platform (518). While FIGS. 17A-17B only show buttress assembly (410) on platform (518), buttress assembly (412) would be retained on and released from platform (518) in an identical fashion. To use cartridge (510) to load end effector (12), the operator would first position cartridge (510) and end effector (12) such that end effector is aligned with open end (512) of cartridge (510) as shown in FIG. 17A. The operator would then advance end effector (12) distally (and/or retract cartridge (510) proximally) to position platform (518) and buttress assemblies (410, 412) between anvil (18) and staple cartridge (37) as shown in FIG. 17B. This will ultimately result in the arrangement shown in FIG. 17A.

V. Exemplary Buttress Applier Cartridges

It may be desirable to use buttress assemblies (410, 412) with end effector (212, 312). However, since end effectors (212, 312) have curved distal tips (219, 314), it may be difficult or impractical to use cartridge (510) to load buttress assemblies (410, 412) on end effectors (212, 312). It may therefore be desirable to provide a modified version of cartridge (510) that accommodates curved distal tips (219, 314), thereby facilitating loading of buttress assemblies (410, 412) on end effectors (212, 312). Examples of such a buttress applier cartridge (610, 710) are described below. While buttress applier cartridges (610, 710) are described in the context of end effector (312), buttress applier cartridges (610, 710) may also be used with end effector (212) and other end effectors that have curved or otherwise deflected distal tip portions.

A. Second Exemplary Buttress Applier Cartridge

Figure 18:
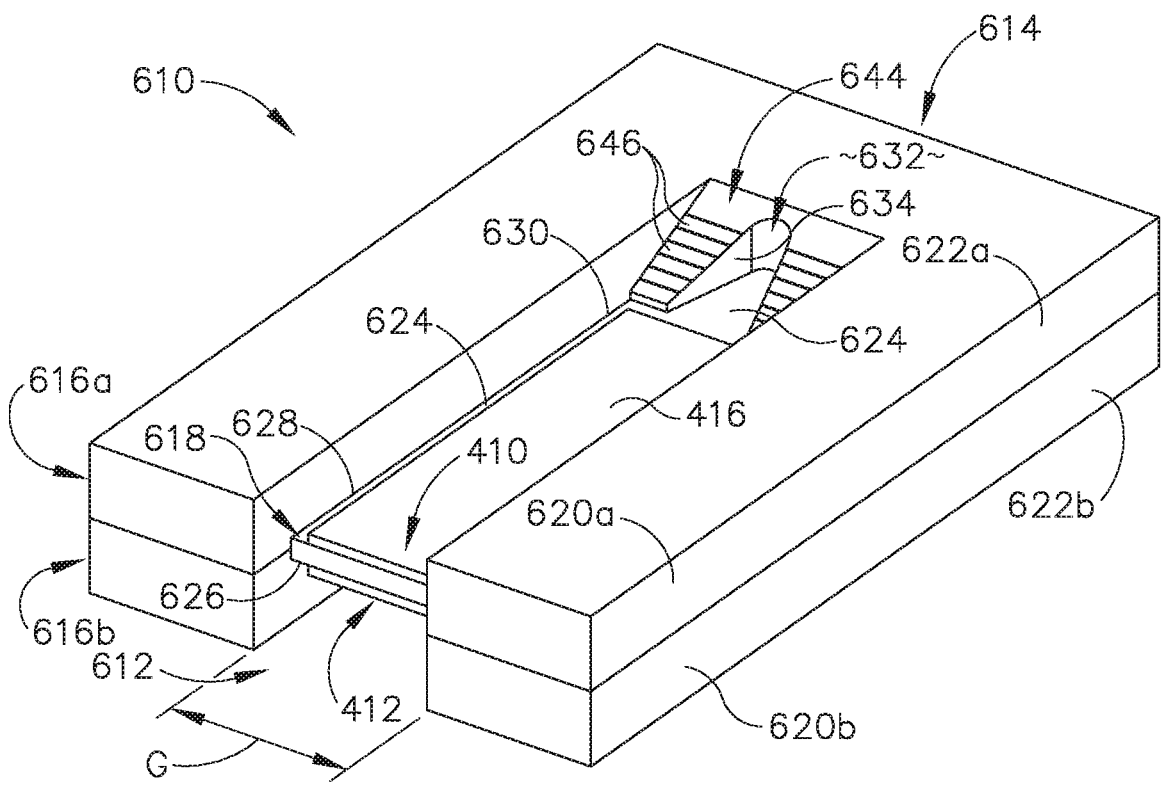
FIG. 18 depicts a schematic perspective view of a second exemplary buttress applier cartridge that may be used to carry and apply the buttress assembly of FIG. 12.

FIGS. 18-20B show a second exemplary buttress applier cartridge (610) that may be used to support and protect buttress assemblies (410, 412). Buttress applier cartridge (610) may also be used to easily load buttress assemblies (410, 412) on end effector (312). As shown in FIG. 18, buttress applier cartridge (610) includes an open end (612) and a closed end (614). Open end (612) is configured to receive end effector (312), in a similar manner as buttress applier cartridge (510) shown in FIGS. 17A-17B. While buttress applier cartridge (610) is described and shown below with relation to instrument (310), end effector (312), placement tip (314), lower jaw (316), anvil (318) and staple cartridge (324), principles are also applicable to other instruments have curved distal tips, such as end effector (212) that includes lower jaw (216), anvil (218), distal tip (219) and staple cartridge (37).

Figure 19:
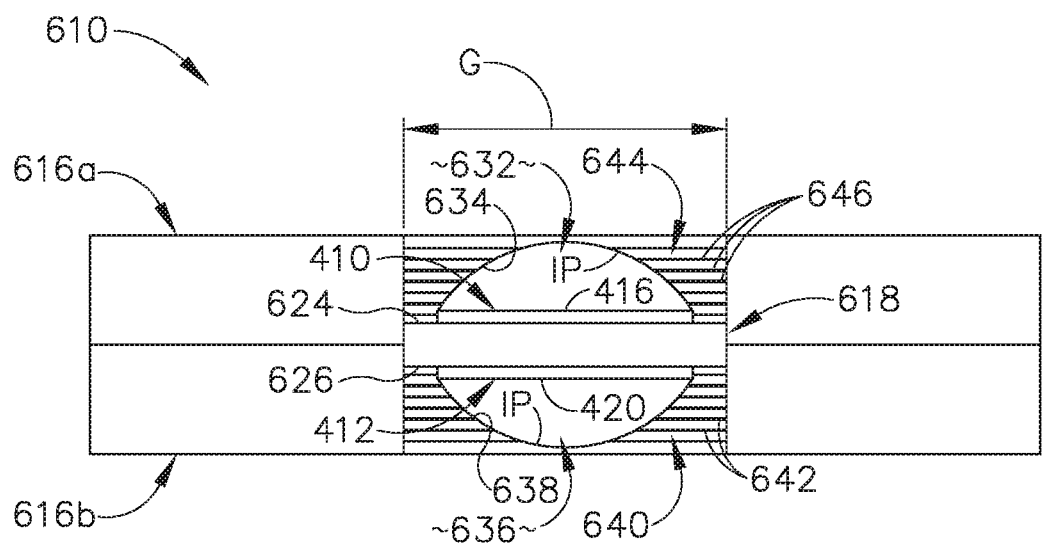
FIG. 19 depicts a schematic front plan view of the buttress applier cartridge of FIG. 18.
Figure 20A:
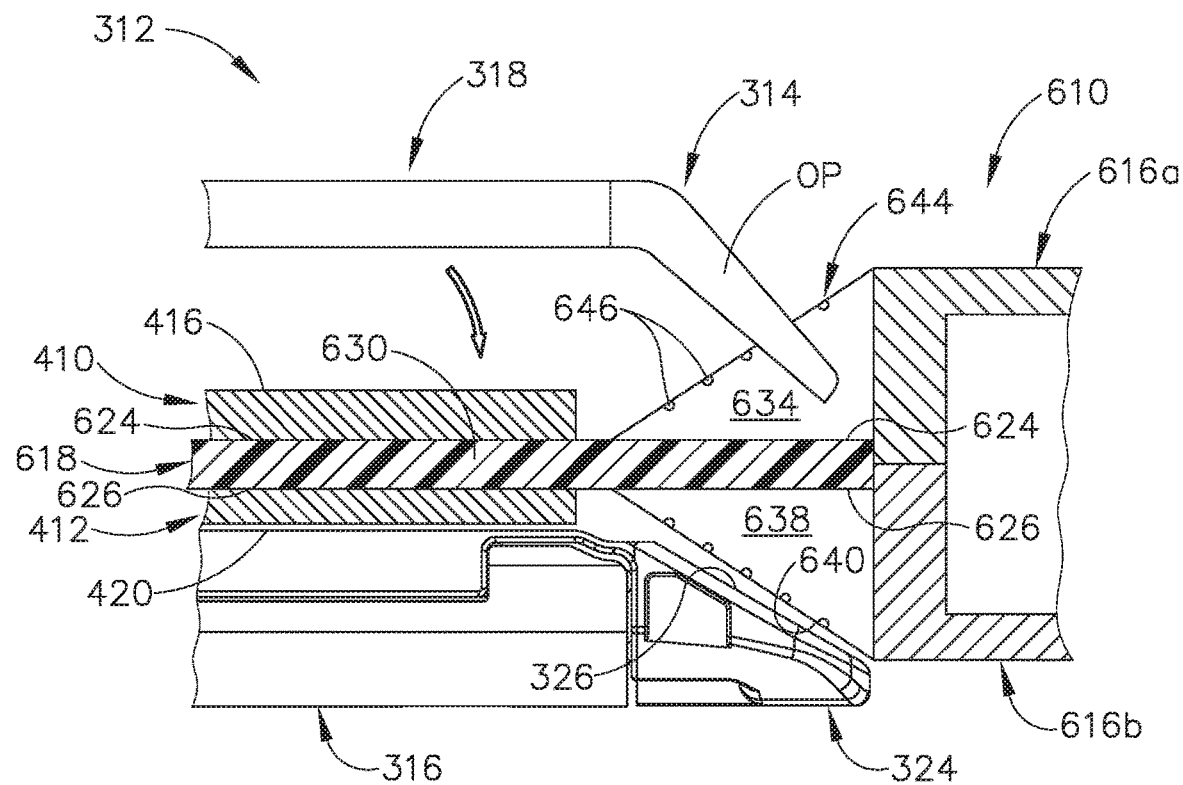
FIG. 20A depicts a schematic cross-sectional side view of the end effector of FIG. 11 and the buttress applier cartridge of FIG. 18, with the buttress applier cartridge positioned in the end effector, and with the end effector in an open configuration.
Figure 20B:
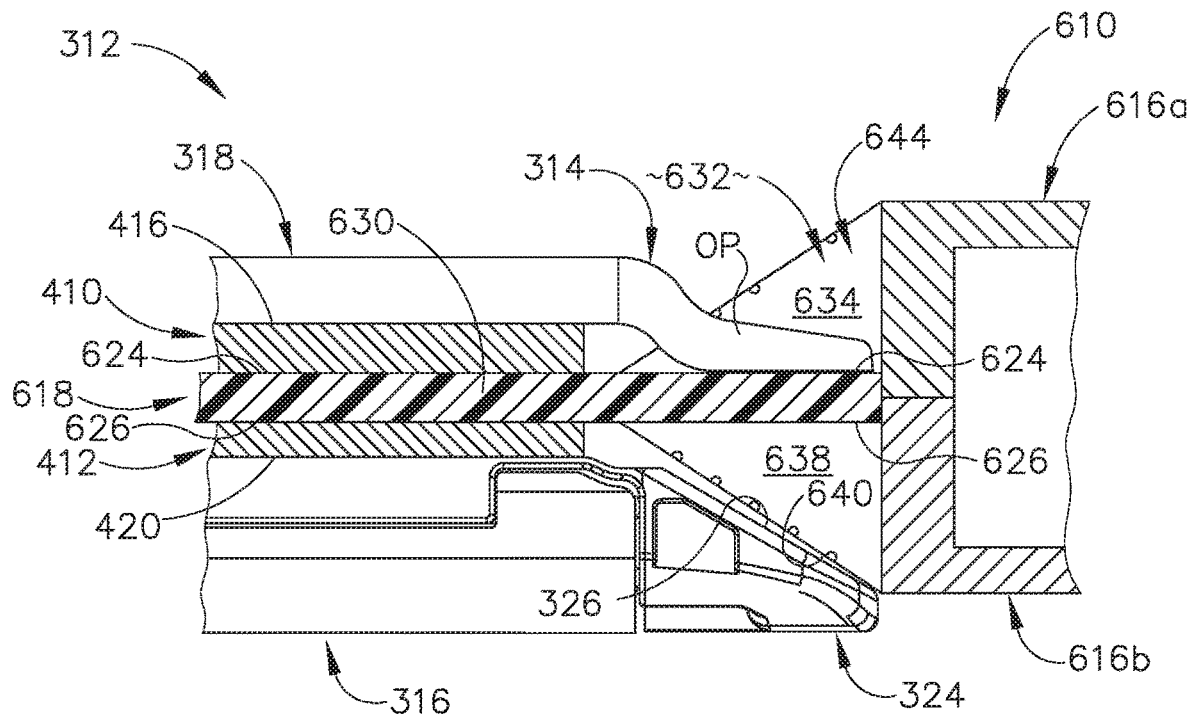
FIG. 20B depicts a schematic cross-sectional side view of the end effector of FIG. 11 and the buttress applier cartridge of FIG. 18, with the buttress applier cartridge positioned in the end effector, and with the end effector in a closed configuration.
Figure 21:
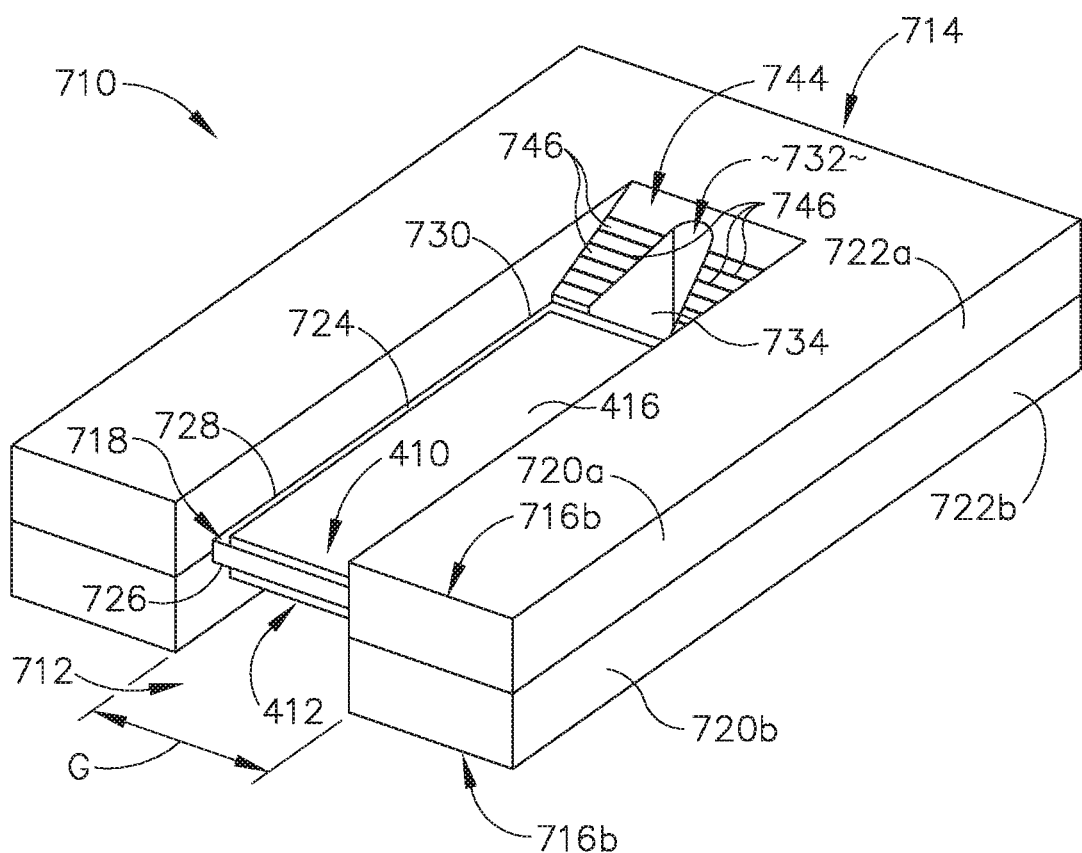
FIG. 21 depicts a schematic perspective view of a third exemplary buttress applier cartridge that may be used to carry and apply the buttress assembly of FIG. 12.

With continued reference to FIG. 18, buttress applier cartridge (610) includes a first housing (616a) and a second housing (616b), with each generally defining a "U" shape to present open end (612). First and second housings (616a-b) define a gap (G) configured to receive a portion of an end effector (312) of a surgical stapler (310). First and second housings (616a-b) receive a platform (618). First housing (616a) includes proximal and distal portions (620a, 622a), while second housing (616b) includes proximal and distal portions (620b, 622b). As shown, first and second housings (616a-b) are separately formed from platform (618) and subsequently coupled with platform (618). Alternatively, first and second housings (616*a-b*) may be integrally formed together as a unitary piece together and subsequently coupled with platform (618), or alternatively, first and second housings (616*a-b*) may be integrally formed together as a unitary piece together with platform (618). As shown, first and second housings (616*a-b*) and platform (618) are symmetric about a plane generally defined by platform (618). In other words, using the spatial orientation of FIG. 19, the left side of the buttress applier cartridge (610) is symmetric to the right side of the buttress applier cartridge (610). Similarly, using the spatial orientation of FIGS. 20A-20B showing distal portions (622*a-b*, 630), the top side of the buttress applier cartridge (610) is symmetric to the bottom side of the buttress applier cartridge (610). The buttress applier cartridge (610) may be non-symmetric if desired.

Platform (618) is configured to support one or more buttress assemblies (400, 410) against a first side (624) (e.g. a top side) of platform (618) and one or more buttress assemblies (412) against a second side (626) (e.g. a bottom side) of platform (618). As shown, platform (618) includes proximal and distal portions (628, 630). Platform (618) is disposed between first and second housings (616*a-b*). A portion of platform (618) is disposed within gap (G) defined by first and second housings (616*a-b*). The location of platform (618) and buttress assemblies (410, 412) in the gap (G) may prevent inadvertent contact between buttress assemblies (410, 412) and other devices in the operating room. In other words, first and second housings (616*a-b*) may provide some degree of physical shielding of buttress assemblies (410, 412). Outer portions of platform (618) may be captured between first and second housings (616*a-b*) to thereby securably couple platform (618) with first and second housings (616*a-b*).

In some versions, platform (618) is formed of a material that provides a high coefficient of friction, thereby reducing any tendency that buttress assemblies (410, 412) might otherwise have to slide along corresponding surfaces of platform (618). For instance, platform (618) may comprise an elastomeric material and/or a foam material. In some instances, platform (618) is formed of a compressible foam material that is configured to maintain a compressed configuration after being compressed by end effector (312). By way of example only, platform (618) may comprise Santoprene, closed-cell polyurethane foam, any other compressible material, and/or a material that may be made compressible via geometry (e.g., a rubber material with deformable standing features). Various suitable materials and structural configurations that may be used to form platform (618) will be apparent to those of ordinary skill in the art in view of the teachings herein.

At least one of distal portion (630) of platform (618) or distal portion (622*a-b*) of first and second housings (616*a-b*) include one or more cavities configured to receive a curved distal tip (314) of a first jaw of end effector (312). As shown in FIGS. 18-20B, first housing (616*a*) includes a first cavity (632) disposed adjacent first side (624) of platform (618). First cavity (632) enables curved distal tip (314) to extend below a staple deck (such as staple deck (72) of staple cartridge (37)) in the closed configuration. First cavity (632) terminates at a top surface of platform (618). As shown, first cavity (632) extends generally perpendicular to platform (618). However, first cavity (632) may extend at various suitable angles relative to platform (618). As shown, first cavity (632) has a cross-sectional area that increases moving towards platform (618). First cavity (632) has an inner perimeter (IP) defined by inner walls (634) that is configured to closely accommodate an outer perimeter (OP) of curved distal tip (314) of end effector (312). As shown, first cavity (632) does not extend across the entire width of gap (G); however, first cavity (632) may extend across the entire width of gap (G) if desired. As shown in FIG. 20B, curved distal tip (314) of end effector (312) is configured to deform against platform (618) when end effector (312) is in the closed configuration.

Since buttress applier cartridge (610) is shown as being symmetric, a second cavity (636) having inner walls (638) is adjacent second side (626) of platform (618). As shown in FIG. 19, second cavity (636) terminates at second side (626) of platform (618). Since first and second cavities (632, 636) have inner perimeter (IP) configured to receive outer perimeter (OP) of placement tip (314), the particular shapes and sizes of first and second cavities (632, 636) may vary to correspond with the desired placement tip (314). As such, it is envisioned that second cavity (636) may be sized and shaped similar to first cavity (632), or alternatively, may be sized and/or shaped differently than first cavity (632), such that second cavity (636) is configured to receive a different placement tip than first cavity (632) if desired.

At least one of distal portion (630) of platform (618) or distal portion (622*a-b*) of housings (616*a-b*) include a surface configured to assist in placement of a staple cartridge (324) of a second jaw of end effector (312). As shown in FIGS. 19-20B, second housing (616*b*) includes a first angled surface (640) formed on an opposing side of first cavity (632). First angled surface (640) extends across gap (G) adjacent second side (626) of platform (618). First angled surface (640) is configured to assist in placement of a second jaw of end effector (212, 312) adjacent second side (626) of platform (618). More specifically, first angled surface (640) is configured to assist in placement of staple cartridge (37, 324). As shown, placement tip (314) is coupled with anvil (318) is disposed opposite lower jaw (316) this is configured to receive staple cartridge (324). First angled surface (640) is in abutting contact with a distal angled portion (326) of staple cartridge (37, 33) when the opposing jaws (such as lower jaw (16) and anvil (18)) are moving towards the closed configuration. Additionally, first angled surface (640) includes ridges (642) if desired.

As shown, first housing (616*a*) includes a second angled surface (644) formed on an opposing side of second cavity (636). Second angled surface (644) extends across gap (G) adjacent first side (624) of platform (618). Second angled surface (644) is configured to assist in placement of a first jaw of end effector (312) adjacent first side (624) of platform (618). More specifically, second angled surface (644) may generally assist in placement of placement tip (314). Second angled surface (644) may include ridges (646).

As shown in FIGS. 18-20B, first buttress assembly (410) is positioned on at least proximal portion (628) of platform (618). First buttress assembly (410) is disposed in gap (G) defined by housings (616*a-b*). As shown in FIG. 19-20B, second buttress assembly (412) is positioned on second side (626) of platform (618). Additionally, as shown with respect to FIGS. 15-17A, buttress assemblies (410, 412) may be provided in a respective pair of portions that are separated at a distance to avoid spanning across slots (42, 49) to support wide versions of buttress assemblies (410, 412) that unitarily span across slots (42, 49) of anvil (18) and staple cartridge (37) referring to instrument (10), respectively.

FIGS. 20A-20B depict an exemplary method of using cartridge (610) to secure buttress assemblies (410, 412) to end effector (312). The method includes positioning platform (618) of buttress applier cartridge (610) between the first and second jaws of end effector (312), such that buttress assembly (410) is below anvil (318) and buttress assembly (412) is above the deck of lower jaw (316), while first and second jaws are in an open configuration. First cavity (632) accommodates curved distal tip (314) during such positioning. The method also includes driving one or both of the first or second jaws of end effector (312) toward platform (618) to thereby engage buttress assemblies (410, 412). As shown in FIG. 20B, as curved distal tip (314) of end effector (312) contacts and subsequently deforms against first side (624) of platform (618) when end effector (312) moves to the closed configuration, the angle of curved distal tip (314) changes. The method also includes driving one or both of the first or second jaws of end effector (312) away from platform (618) to thereby pull buttress assemblies (410, 412) off of platform (618).

B. Third Exemplary Buttress Applier Cartridge

Figure 22:
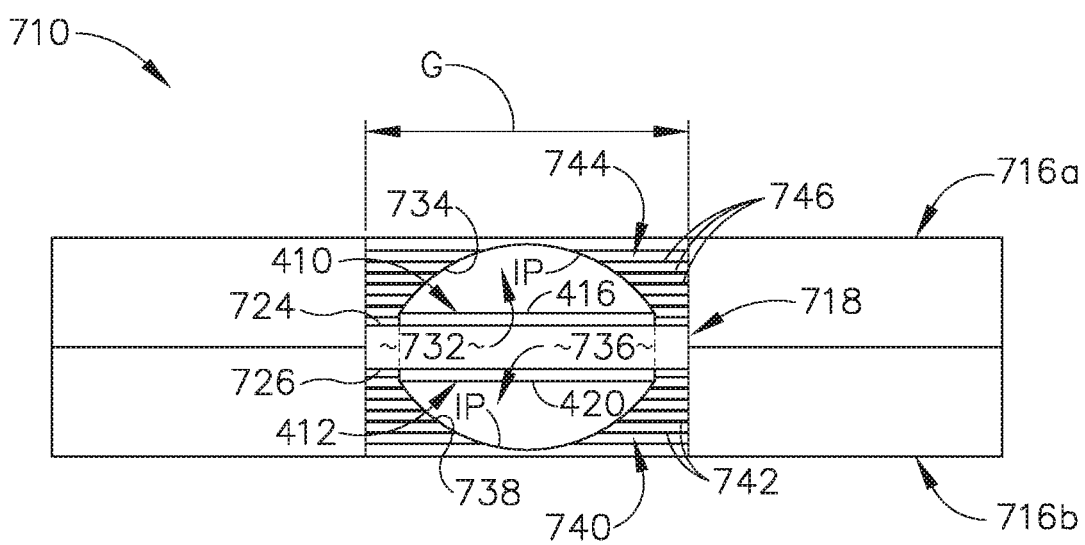
FIG. 22 depicts a schematic front plan view of the buttress applier cartridge of FIG. 21.
Figure 23A:
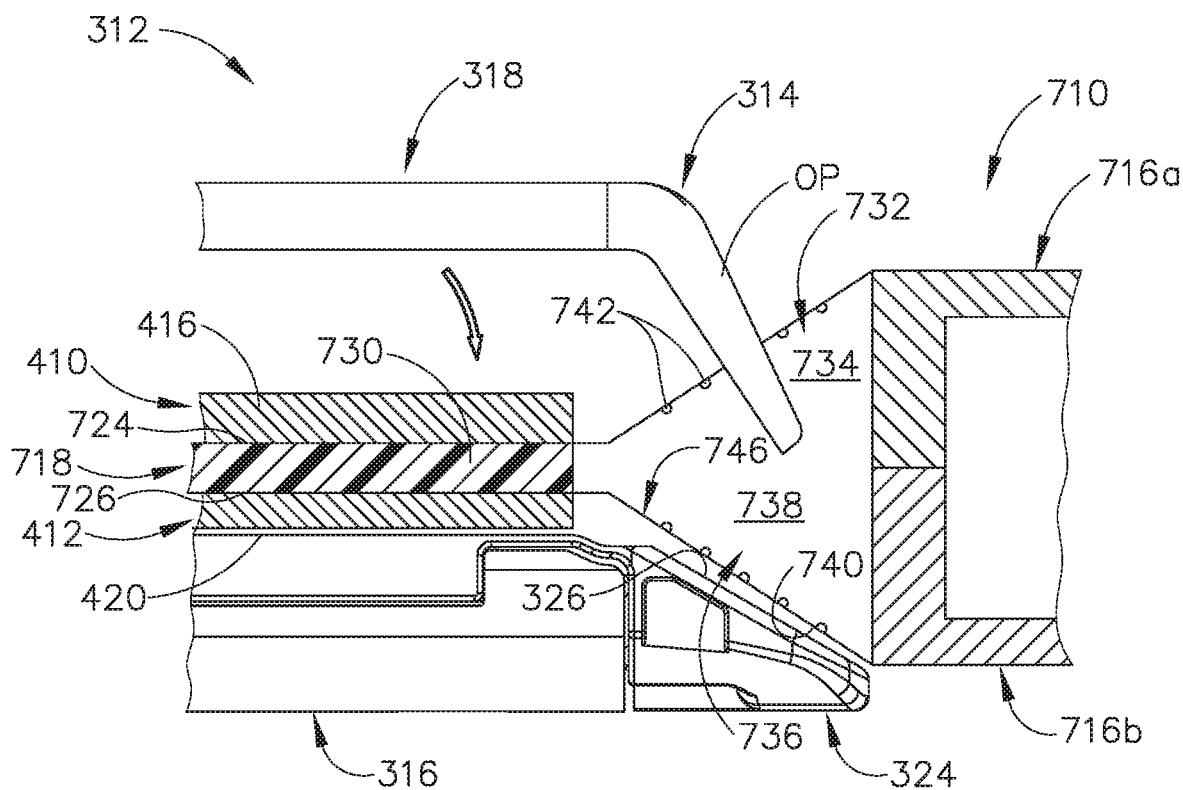
FIG. 23A depicts a schematic cross-sectional side view of the end effector of FIG. 11 and the buttress applier cartridge of FIG. 21, with the buttress applier cartridge positioned in the end effector, and with the end effector in an open configuration.
Figure 23B:
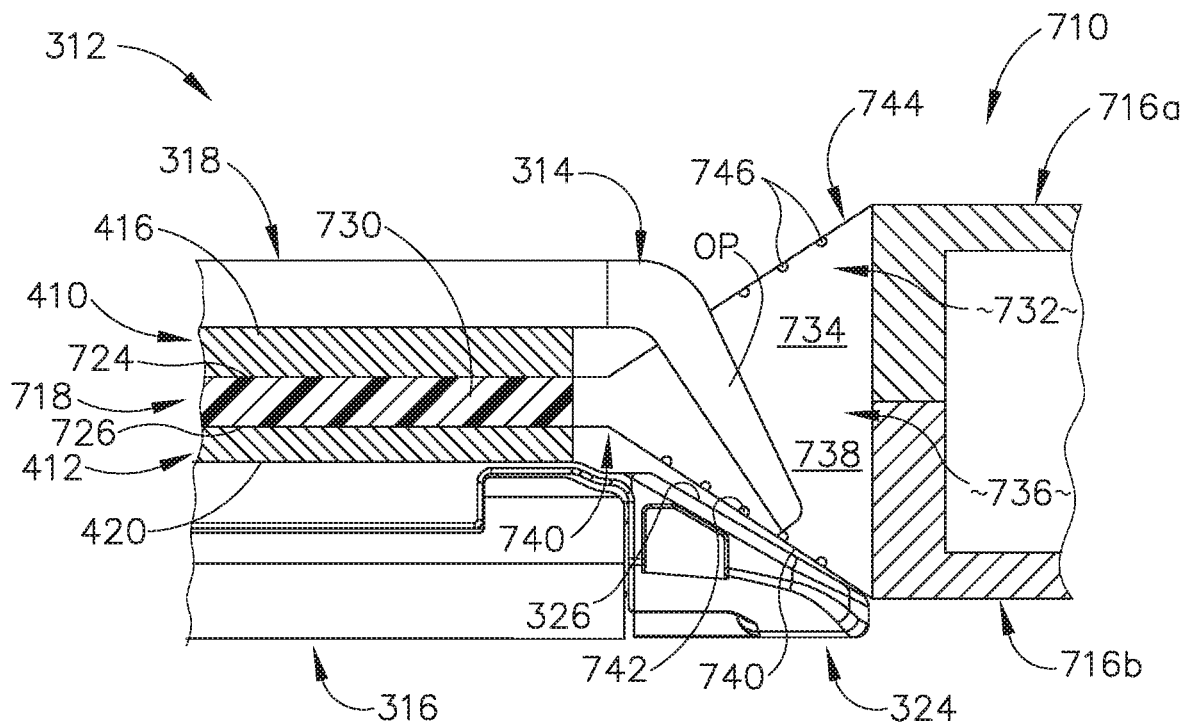
FIG. 23B depicts a schematic cross-sectional side view of the end effector of FIG. 11 and the buttress applier cartridge of FIG. 21, with the buttress applier cartridge positioned in the end effector, and with the end effector in a closed configuration.

FIGS. 22-23B show a third exemplary buttress applier cartridge (710). Like buttress applier cartridge (610), buttress applier cartridge (710) of this example may be used with any end effector (12, 312, 412) described herein and in any of the various procedures described in the various patent references cited herein. Buttress applier cartridge (710) is configured and operable just like buttress applier cartridge (610), except for the differences indicated below.

Buttress applier cartridge (710) includes an open end (712), a closed end (714), a first housing (716a), a second housing (716b), a platform (718), proximal portions (720a, 720b) of first and second housings (716a, 716b), distal portions (722a, 722b) of first and second housings (716a, 716b), a first side (724), a second side (726), a proximal portion (728) of platform (718), a distal portion (730) of platform (718), a first cavity (732), inner walls (734), a second cavity (736), inner walls (738), a first angled surface (740), ridges (742), a second angled surface (744), and ridges (746). To this end, like numbers below indicate like features described above. Except as otherwise described below, certain details of buttress applier cartridge (710) will therefore be omitted from the following description, it being understood that such details are already provided above in the description of buttress applier cartridge (610). Other suitable ways in which various buttress applier cartridges may be used will be apparent to those of ordinary skill in the art in view of the teachings herein.

As shown in FIGS. 22-23B, first and second cavities (732, 736) connect, and therefore, extend completely through platform (718). In other words, first and second cavities (732, 736) extend completely through first and second sides (724, 726) of platform (718), defining a passageway that passes through the full thickness of cartridge (710). First and second cavities (732, 736) extending completely therethrough platform (718) allow placement tip (314) to maintain its curved shape and not deform against platform (718) when end effector (312) is in the closed configuration as shown in FIG. 23B. Buttress applier cartridge (710) may thus be used for versions where distal tip (219) or placement tip (314) is rigid; or when it is desired that distal tip (219) or placement tip (314) not deflect.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing defining a gap configured to receive a portion of an end effector of a surgical stapler, wherein the housing includes proximal and distal portions; (b) a platform, wherein a portion of the platform is exposed within the gap defined by the housing, wherein the platform includes proximal and distal portions; and (c) a first buttress assembly positioned on at least the proximal portion of the platform, wherein the first buttress assembly is exposed in the gap defined by the housing, wherein at least one of the distal portion of the platform or the distal portion of the housing includes a cavity configured to receive a curved distal tip of the end effector.

Example 2

The apparatus of Example 1, wherein the cavity terminates at a top surface of the platform, wherein the curved distal tip of the end effector is configured to deform against the platform when the end effector is in the closed configuration.

Example 3

The apparatus of any one or more of Examples 1 through 2, wherein the cavity extends completely through the platform, wherein the curved distal tip of the end effector is configured maintain its curved shape and not deform against the platform when the end effector is in the closed configuration on the platform.

Example 4

The apparatus of any one or more of Examples 1 through 3, wherein the curved distal tip is configured to extend below a staple deck of the opposing staple cartridge of the end effector in the closed configuration.

Example 5

The apparatus of any one or more of Examples 1 through 4, wherein the cavity extends perpendicular to the platform, and wherein the cavity has a cross-sectional area that increases moving towards the platform.

Example 6

The apparatus of any one or more of Examples 1 through 5, wherein an inner perimeter of the cavity has is configured to closely accommodate an outer perimeter the curved distal tip of the end effector.

Example 7

The apparatus of any one or more of Examples 1 through 6, wherein the cavity does not extend across the entire width of the gap.

Example 8

The apparatus of any one or more of Examples 1 through 7, wherein the apparatus is symmetric about a plane defined by the platform.

Example 9

The apparatus of any one or more of Examples 1 through 8, wherein the end effector includes first and second opposing jaws, wherein the first jaw includes the curved distal tip and the second jaw includes a staple cartridge, wherein the proximal portion of the platform is configured to be between the first and second opposing jaws.

Example 10

The apparatus of any one or more of Examples 1 through 9, wherein the end effector includes first and second opposing jaws, wherein the first jaw includes the curved distal tip and the second jaw includes a staple cartridge, wherein the distal portion of the housing or the distal portion of the platform includes a first angled surface that is configured to be in abutting contact with a distal angled portion of the staple cartridge.

Example 11

The apparatus of any one or more of Examples 1 through 10, wherein the platform includes first and second opposing sides, wherein the cavity is adjacent the first side and the first angled surface is adjacent the second side, wherein the first angled surface is configured to assist in placement of the staple cartridge.

Example 12

The apparatus of any one or more of Examples 1 through 11, wherein the first buttress assembly comprises: (i) a body, and (ii) an adhesive layer, wherein the adhesive layer is exposed in the gap defined by the housing.

Example 13

The apparatus of any one or more of Examples 1 through 12, further comprising a second buttress assembly, wherein the first buttress assembly is positioned on a first side of the platform and the second buttress assembly is positioned on a second side of the platform disposed opposite the first side.

Example 14

The apparatus of any one or more of Examples 1 through 13, wherein the housing is integrally formed together as a unitary piece together with the platform.

Example 15

The apparatus of any one or more of Examples 1 through 14, wherein the housing is separately formed from and subsequently coupled with the platform.

Example 16

An apparatus comprising: (a) a housing defining a gap configured to receive a portion of an end effector of a surgical stapler, wherein the housing includes proximal and distal portions; (b) a platform including first and second opposing sides, wherein a portion of the platform is exposed within the gap defined by the housing, wherein the platform includes proximal and distal portions; and (c) a first buttress assembly positioned on the first side of the platform, wherein the first buttress assembly is exposed within the gap defined by the housing, wherein at least one of the distal portion of the platform or the distal portion of the housing includes a cavity adjacent the first side of the platform, wherein the cavity is configured to receive a curved distal tip of a first jaw of the end effector, and wherein at least one of the distal portion of the platform or the distal portion of the housing includes an angled surface extending across the gap adjacent the second side of the platform, wherein the angled surface is configured to assist in placement of a staple cartridge of a second jaw of the end effector adjacent the second side of the platform.

Example 17

The apparatus of any one or more of Examples 1 through 16, further comprising a second buttress assembly on the second side of the platform, wherein the second buttress assembly is exposed in the gap defined by the housing.

Example 18

The apparatus of any one or more of Examples 1 through 17, wherein the cavity terminates at a planar surface of the platform, wherein the curved distal tip of the end effector is configured to deform against the platform when the end effector is in the closed configuration.

Example 19

The apparatus of any one or more of Examples 1 through 18, wherein the cavity extends completely through the platform, wherein the curved distal tip of the end effector is configured to maintain its curved shape and not deform against the platform when the end effector is in the closed configuration.

Example 20

A method of securing a buttress assembly to an end effector having first and second opposing jaws, the method comprising: (a) positioning a platform of a buttress applier cartridge between the first and second jaws while the first and second jaws are in an open configuration, wherein the platform has a buttress disposed thereon; (b) driving one or both of the first and second jaws toward the platform to thereby engage the buttress assembly with one of the first and second jaws, wherein a distal portion of the buttress applier cartridge includes a cavity that is sized and shaped to receive a curved distal tip of one of the first or second jaws, wherein the curved distal tip extends beyond a staple deck of a staple cartridge of the other of first or second jaws when in the closed configuration; and (c) driving one or both of the first or second jaws away from the platform to thereby pull the buttress assembly off of the platform.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Patent Pub. No. 2017/0055981, entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein. Various suitable ways in which the teachings herein may be combined with the teachings of U.S. Patent Pub. No. 2017/0055981, issued as U.S. Pat. No. 10,166,023 on Jan. 1, 2019, will be apparent to those of ordinary skill in the art.

It should also be understood that the teachings herein may be readily combined with various teachings in U.S. Patent Pub. No. 2018/0325516, entitled "Method of Surgical Stapling with End Effector Component Having a Curved Tip," published Nov. 15, 2018, the disclosure of which is incorporated by reference herein. Various suitable ways in which the teachings herein may be combined with the teachings of U.S. Patent Pub. No. 2018/0325516 will be apparent to those of ordinary skill in the art.

It should also be understood that the teachings herein may be readily combined with various teachings in U.S. Patent Pub. No. 2018/0325515, entitled "Surgical Stapling End Effector Jaw with Tip Deflecting Toward Other Jaw," published Nov. 15, 2018, the disclosure of which is incorporated by reference herein. Various suitable ways in which the teachings herein may be combined with the teachings of U.S. Patent Pub. No. 2018/0325515 will be apparent to those of ordinary skill in the art.

It should also be understood that the teachings herein may be readily combined with various teachings in U.S. Patent Pub. No. 2018/0325514, entitled "Surgical Stapling End Effector Component with Tip Having Varying Bend Angle," published Nov. 15, 2018, the disclosure of which is incorporated by reference herein. Various suitable ways in which the teachings herein may be combined with the teachings of U.S. Patent Pub. No. 2018/0325514 will be apparent to those of ordinary skill in the art.

It should also be understood that the teachings herein may be readily combined with various teachings in U.S. Patent Pub. No. 2020/0015815, entitled "Permanent Attachment Means for Curved Tip of Component of Surgical Stapling Instrument," published Jan. 16, 2020, the disclosure of which is incorporated by reference herein. Various suitable ways in which the teachings herein may be combined with the teachings of U.S. Patent Pub. No. 2020/0015815 will be apparent to those of ordinary skill in the art.

It should also be understood that the teachings herein may be readily combined with various teachings in U.S. Patent Pub. No. 2020/0015811, entitled "Surgical Stapling End Effector Component with Deformable Tip Having Void," published Jan. 16, 2020, issued as U.S. Pat. No. 10,786,252 on Sep. 29, 2020, the disclosure of which is incorporated by reference herein. Various suitable ways in which the teachings herein may be combined with the teachings of U.S. Patent Pub. No. 2020/0015811, issued as U.S. Pat. No. 10,786,252 on Sep. 29, 2020, will be apparent to those of ordinary skill in the art.

It should also be understood that the teachings herein may be readily combined with various teachings in U.S. Patent Pub. No. 2020/0015812, entitled "Surgical Stapling End Effector Component with Deformable Tip Skewing in Multiple Planes," published Jan. 16, 2020, the disclosure of which is incorporated by reference herein. Various suitable ways in which the teachings herein may be combined with the teachings of U.S. Patent Pub. No. 2020/0015812 will be apparent to those of ordinary skill in the art.

It should also be understood that the teachings herein may be readily combined with various teachings in U.S. Patent Pub. No. 2020/0015813, entitled "Surgical Stapling End Effector Component with Articulation and Asymmetric Deformable Tip," published Jan. 16, 2020, the disclosure of which is incorporated by reference herein. Various suitable ways in which the teachings herein may be combined with the teachings of U.S. Patent Pub. No. 2020/0015813 will be apparent to those of ordinary skill in the art.

It should also be understood that the teachings herein may be readily combined with various teachings in U.S. Patent Pub. No. 2020/0015814, entitled "Surgical Stapling End Effector Component with Deformable Tip Having Thick Distal End," published Jan. 16, 2020, the disclosure of which is incorporated by reference herein. Various suitable ways in which the teachings herein may be combined with the teachings of U.S. Patent Pub. No. 2020/0015814 will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a housing defining a gap configured to receive a portion of an end effector of a surgical stapler, wherein the housing includes proximal and distal portions;
   (b) a platform coupled with the housing, wherein a portion of the platform is exposed within the gap defined by the housing, wherein the platform includes proximal and distal portions; and
   (c) a first buttress assembly positioned on at least the proximal portion of the platform, wherein the first buttress assembly is exposed in the gap defined by the housing,
   wherein at least one of the distal portion of the platform or the distal portion of the housing includes a cavity extending distally beyond the gap, wherein the cavity extends completely through the platform such that the cavity is configured to receive a curved distal tip of the end effector.

2. The apparatus of claim 1, wherein the curved distal tip of the end effector is configured maintain its curved shape and not deform against the platform when the end effector is in the closed configuration on the platform.

3. The apparatus of claim 2, wherein the curved distal tip is configured to extend below a staple deck of the opposing staple cartridge of the end effector in the closed configuration when received within the cavity.

4. The apparatus of claim 1, wherein the cavity extends perpendicular to the platform, and wherein the cavity has a cross-sectional area that increases moving towards the platform.

5. The apparatus of claim 1, wherein an inner perimeter of the cavity is configured to closely accommodate an outer perimeter the curved distal tip of the end effector.

6. The apparatus of claim 1, wherein the cavity does not extend across the entire width of the gap.

7. The apparatus of claim 1, wherein the apparatus is symmetric about a plane defined by the platform.

8. The apparatus of claim 1, wherein the end effector includes first and second opposing jaws, wherein the first jaw includes the curved distal tip and the second jaw includes a staple cartridge, wherein the proximal portion of the platform is configured to be between the first and second opposing jaws.

9. The apparatus of claim 1, wherein the end effector includes first and second opposing jaws, wherein the first jaw includes the curved distal tip and the second jaw includes a staple cartridge, wherein the distal portion of the housing or the distal portion of the platform includes a first angled surface that is configured to be in abutting contact with a distal angled portion of the staple cartridge.

10. The apparatus of claim 9, wherein the platform includes first and second opposing sides, wherein the cavity is adjacent the first side and the first angled surface is adjacent the second side, wherein the first angled surface is configured to assist in placement of the staple cartridge.

11. The apparatus of claim 1, wherein the first buttress assembly comprises:
   (i) a body, and
   (ii) an adhesive layer, wherein the adhesive layer is exposed in the gap defined by the housing.

12. The apparatus of claim 1, further comprising a second buttress assembly, wherein the first buttress assembly is positioned on a first side of the platform and the second buttress assembly is positioned on a second side of the platform disposed opposite the first side.

13. An apparatus comprising:
   (a) a housing defining a gap configured to receive a portion of an end effector of a surgical stapler, wherein the housing includes proximal and distal portions;
   (b) a platform coupled with the housing, wherein the platform includes first and second opposing sides, wherein a portion of the platform is exposed within the gap defined by the housing, wherein the platform includes proximal and distal portions; and
   (c) a first buttress assembly positioned on the first side of the platform, wherein the first buttress assembly is exposed within the gap defined by the housing,
   wherein at least one of the distal portion of the platform or the distal portion of the housing includes a cavity adjacent the first side of the platform, wherein the cavity extends distally beyond the gap, wherein the cavity is configured to receive a curved distal tip of a first jaw of the end effector, and
   wherein at least one of the distal portion of the platform or the distal portion of the housing includes an angled surface extending across the gap adjacent the second side of the platform, wherein the angled surface is configured to assist in placement of a staple cartridge disposed on a second jaw of the end effector adjacent the second side of the platform.

14. The apparatus of claim 13, further comprising a second buttress assembly on the second side of the platform, wherein the second buttress assembly is exposed in the gap defined by the housing.

15. The apparatus of claim 13, wherein the cavity extends completely through the platform, wherein the curved distal tip of the end effector is configured to maintain its curved shape and not deform against the platform when the end effector is in the closed configuration.

16. The apparatus of claim 13, wherein the cavity extends through a portion of the angled surface.

17. The apparatus of claim 13, wherein an inner perimeter of the cavity is configured to closely accommodate an outer perimeter the curved distal tip of the end effector.

18. A method of securing a buttress assembly to an end effector having first and second opposing jaws, the method comprising:
   (a) positioning a platform of a buttress applier cartridge between the first and second jaws while the first and second jaws are in an open configuration, wherein the platform has a buttress disposed thereon;
   (b) driving one or both of the first and second jaws toward the platform to thereby engage the buttress assembly with one of the first and second jaws, wherein a distal portion of the buttress applier cartridge includes a cavity extending distally beyond the gap, wherein the cavity is sized and shaped to receive a curved distal tip of one of the first or second jaws, wherein the curved distal tip extends beyond a staple deck of a staple cartridge of the other of first or second jaws when in the closed configuration; and
   (c) driving one or both of the first or second jaws away from the platform to thereby pull the buttress assembly off of the platform.

19. The method of claim 18, wherein driving one or both of the first and second jaws toward the platform further comprises receiving the curved distal tip within the cavity that extends completely through the platform such that the curved distal tip maintain its curved shape and does not deform against the platform when the end effector is in the closed configuration on the platform.

\* \* \* \* \*